US008642534B2

(12) United States Patent
Yildiz

(10) Patent No.: US 8,642,534 B2
(45) Date of Patent: Feb. 4, 2014

(54) **PROTEINS AND POLYNUCLEOTIDES OF *VIBRIO CHOLERAE***

(75) Inventor: Fitnat Yildiz, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 691 days.

(21) Appl. No.: 12/087,825

(22) PCT Filed: Jan. 16, 2007

(86) PCT No.: PCT/US2007/001131

§ 371 (c)(1), (2), (4) Date: Apr. 1, 2010

(87) PCT Pub. No.: WO2008/018903
PCT Pub. Date: Feb. 14, 2008

(65) Prior Publication Data

US 2011/0003734 A1 Jan. 6, 2011

Related U.S. Application Data

(60) Provisional application No. 60/758,753, filed on Jan. 14, 2006, provisional application No. 60/860,148, filed on Nov. 20, 2006.

(51) Int. Cl.

| | |
|---|---|
| *A61K 38/00* | (2006.01) |
| *A61K 31/7105* | (2006.01) |
| *G01N 33/53* | (2006.01) |
| *C07H 21/04* | (2006.01) |
| *C07K 14/28* | (2006.01) |
| *C07K 16/12* | (2006.01) |
| *A61P 31/04* | (2006.01) |

(52) U.S. Cl.
USPC ........... 514/2.8; 536/23.7; 436/501; 530/350; 530/389.5

(58) Field of Classification Search
None
See application file for complete search history.

(56) References Cited

PUBLICATIONS

Fong et al. Identification and Characterization of RbmA, a Novel Protein Required for the Development of Rugose Colony Morphology and Biofilm Structure in *Vibrio cholerae*. Journal of Bacteriology. Nov. 2005.*
Tischler et al. Cyclic Diguanylate (c-di-GMP) Regulates *Vibrio cholerae* Biofilm Formation. Mol Microbiol 53(3): 857-869. Aug. 2004.*
Yildiz et al. Molecular Microbiology 2004. Molecular analysis of rugosity in a *Vibrio cholerae* O1 E1 Tor phase variant , 53(2): 497-515.*
Sudha et al., Molecular Microbiology (2005) 57(6): 1623-1635, Identification of Novel Stage-Specific Genetic Requirements Through Whole Genome Transcription Profiling of *Vibrio cholera* Biofilm Development.*
Akhtar Oral Delivery of siRNA and antisense oligonucleotides Jul. 2009.*
Fong et al. The rbmBCDEF Gene Cluster Modulates Development of Rugose Colony Morphology and Biofilm Formation in *Vibrio cholerae*. Jan. 2007.*
Tischler et al. Cyclic Diguanylate (c-di-GMP) Regulates *Vibrio cholerae* Biofilm Formation. 2004.*

* cited by examiner

*Primary Examiner* — Scott Long
*Assistant Examiner* — Sarah Alawadi
(74) *Attorney, Agent, or Firm* — Adam Warwick Ball; Matthew Ruper Kaser

(57) ABSTRACT

Therapeutic, diagnostic and environmental monitoring methods employing proteins encoded by the rbmBCDEF gene cluster and by bap1.

13 Claims, 6 Drawing Sheets

Figures 2, 2A, 2B:
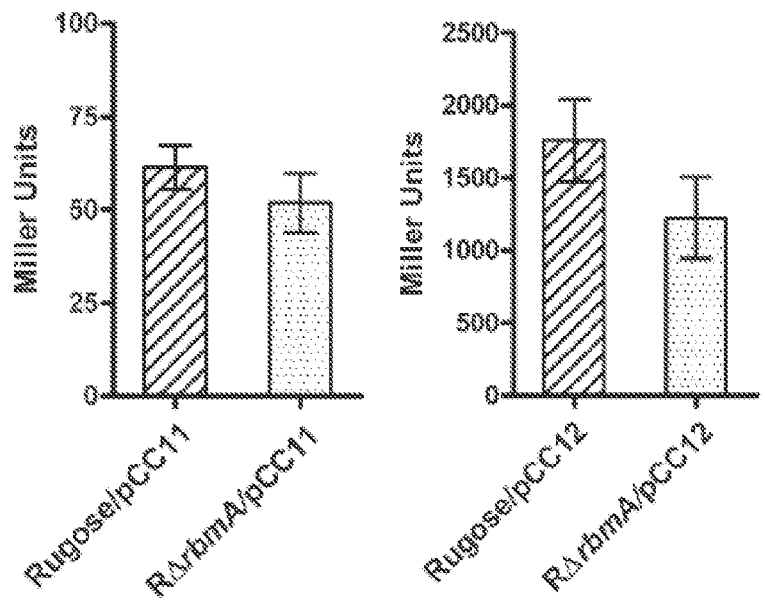

```
VC0928           1   MGNFKGSIMNKRHYYLASCLALLFSTASYAEVDCELQPVI
Protein spot 1       ----------------------------------------

VC0928           41  EANLSLNQNQLASNGGYISSQLGIRNESCETVKFKYWLSI
Protein spot 1       ----------------------------------------

VC0928           81  KGPEGIYFPAKAVVGVPTAQQSSDALFDGRNLSVTRGFWV
Protein spot 1       ----------------------------------------

VC0928           121 PEYMADGKYTVSLQVVAENGKVFKANQEFVKGVDLNSLPE
Protein spot 1       ----------------------------------------

VC0928           161 LNGLTIDIKNQFGINSVESTGGFVPFTVDLMNGREGEANV
Protein spot 1 1     -----------------------------------EGEANV VC0928           201 EFWMTAVGPDGLIIPVNAREKWVIASGDTYSKVRGINFDK
Protein spot 1 7     EFWMTA----------------------------------

VC0928           241 SYPAGEYTINAQVVDIVSGERVEQSMTVVKK
Protein spot 1 12    -------------------------------
```

Fig 1.

```
VC0928         1    MSNFTGSIMNKRHYYLASCLALLFSTASYASVDCELQFVI
Protein spot 1      ----------------------------------------

VC0928         41   EANLSLNQNQLASNGGYISSQLGIRNESCETVKFKYWLSI
Protein spot 1      ----------------------------------------

VC0928         81   KGPEGIYFPAKAVVGVDTAQQESDALTDSPMLSVTRGFWV
Protein spot 1      ----------------------------------------

VC0928         121  PEYMADGKYTVSLQVVAENGKVFKANQEFVKGVDLNSLPE
Protein spot 1      ----------------------------------------

VC0928         161  LNGLTIDIKNQFGINSVESTGGFVPFTVDLNNGREGEANV
Protein spot 1   1  ----------------------------------EGEANV VC0928         201  EFKMTAVGPDGLIIPVNAREKNVIASGDTYSKVRGINFDK
Protein spot 1   7  EFWMTA----------------------------------

VC0928         241  SYPAGEYTINAQVVDIVSGERVEQSMTVVKK
Protein spot 1   12 -------------------------------
```

Fig 1A.

Fig 1B.

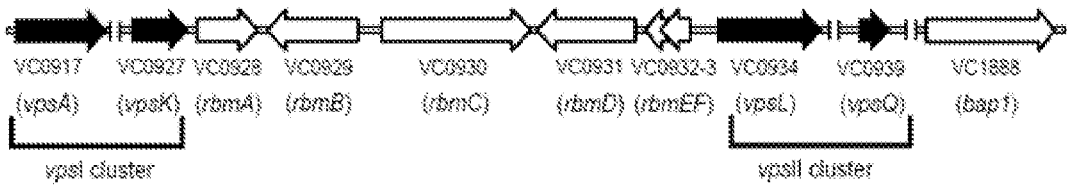

Fig 1C.

Fig. 5
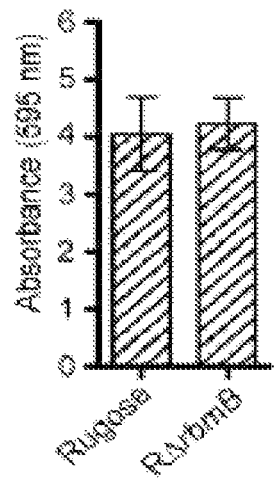
Fig. 6
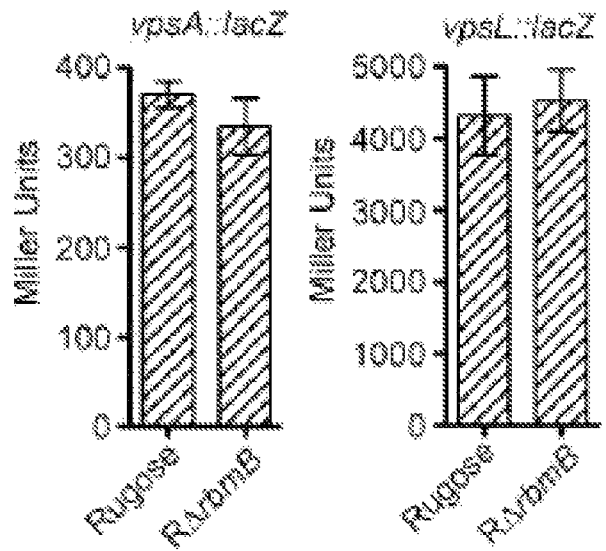
Fig. 6A          Fig. 6B

Fig. 7
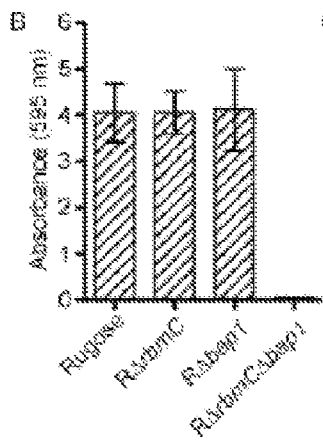 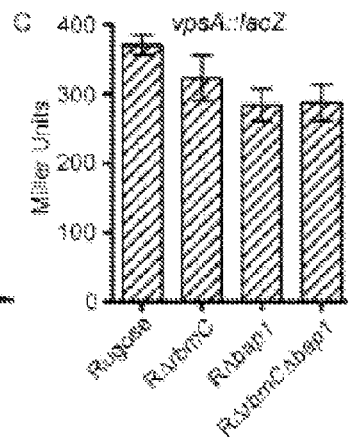 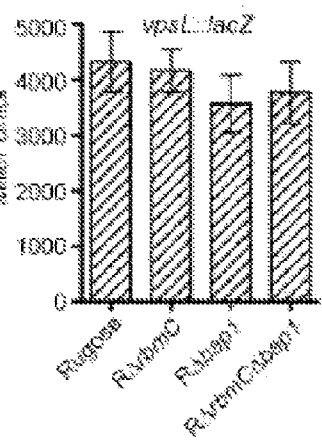
Fig. 7A                Fig. 7B                Fig. 7C
Fig. 8
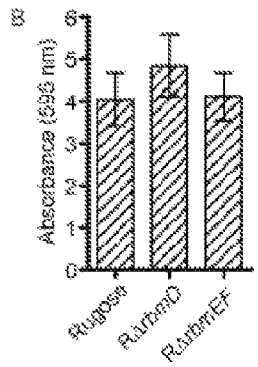 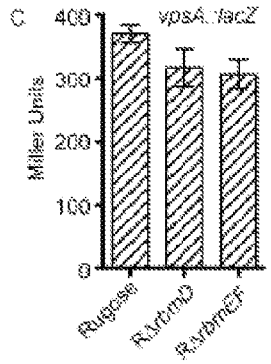 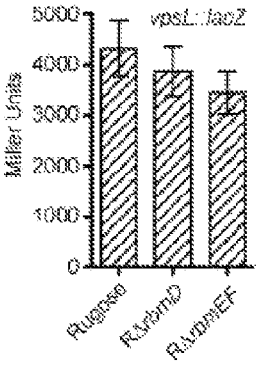
Fig. 8A                Fig. 8B                Fig. 8C

PROTEINS AND POLYNUCLEOTIDES OF VIBRIO CHOLERAE

RELATIONSHIP TO OTHER APPLICATIONS

This application is related to and claims priority from U.S. provisional application No. 60/758,753, filed 14, Jan. 2006, and to U.S. provisional application No. 60/860,148, filed 20 Nov. 2006, both of which are herein incorporated by reference for all purposes.

FIELD OF THE INVENTION

The invention relates to *Vibrio cholefrae*, Rbm (rugosity and biofilm structure modulator) proteins and the rbm polynucleotides and genes that encode them.

BACKGROUND

*Vibrio cholerae*, the etiologic agent of *cholera*, is found naturally in environmental aquatic habitats both as a free-living organism and in a biofilm state attached to different surfaces, including mucilaginous surfaces of phytoplankton, chitinous surfaces of zooplankton and abiotic surfaces. It has been proposed that this facultative human pathogen uses biofilm formation and phenotypic variation as survival strategies which may be related to pathogenicity (Yildiz, F. H., and G. K. Schoolnik. 1999, Proc. Natl. Acad. Sci. USA 96:4028-4033). Biofilms are surface-attached microbial communities composed of microorganisms and the extra-polymeric substances they produce. After initial attachment, colonization of a surface is mediated by the movement and growth of attached bacteria, followed by the formation of microcolonies, which are often surrounded by extra-polymeric substances. Further growth of bacteria and continued production of exopolysaccharides (EPS) lead to the development of mature biofilms characterized by pillars and mushroom-like structures. In *V. cholerae*, the mannose-sensitive hemagglutinin type IV pilus (MSHA) and flagellum facilitate attachment to abiotic surfaces, and *Vibrio*, polysaccharide (VPS), which is part of the extracellular matrix, is required for the development of mature biofilms (Yildiz and G Schoolnik 1999, Proc. Natl. Acad. Sci. USA 96:4028-4033). Cells in the mature biofilms can return back to planktonic stage through detachment, thus completing the cycle. Polysaccharide lyases have been reported to be involved in biofilm detachment and cell dispersal in several biofilm-forming microorganisms.

*V. cholerae*, can undergo phenotypic variation in response to environmental stresses, resulting in rugose and smooth colonial variants (White 1938, J. Pathol. 46:1-6;, Yildiz and Schoolnik 1999 Proc. Natl. Acad. Sci. USA 96:4028-4033). Compared to the smooth variant, the rugose variant forms corrugated colonies, well-developed biofilms and exhibits increased levels of resistance to osmotic and oxidative stresses. Most of these rugose-associated phenotypes are due in part to increased production of VPS, which is mediated by proteins encoded by the vps genes [vpsA-K, VC0917-27, (vpsI cluster); vpsL-Q, VC0934-9, (vpsII cluster)] (FIG. 1). Mutations in any of the vps genes yield smooth colonial morphology and reduced capacity to form biofilms (Yildiz et al, 1999). The vps genes are organized into vpsI (11.5, kb) and vpsII (6.6, kb) coding regions on the large chromosome, separated by an 8.3, kb intergenic region (FIG. 1).

BRIEF DESCRIPTION OF THE INVENTION

The invention encompasses compositions and methods relating to genes and proteins involved in colonization and pathogenesis of *Vibrio cholerae*, particularly rbmA, rbmB, rbmC, rbmD, rbmE, rbmF and Bap1 and variants thereof. The invention relates to diagnostic, therapeutic, and environmental monitoring methods and devices and compositions, particularly for diagnosing, treating, and monitoring the presence of *Vibrio cholera*, . The invention also includes methods and compositions for reducing and preventing the formation of biofilm colonies, and thereby reducing colonization of both biotic and abiotic surfaces, and reducing the spread and pathogenesis of *V. cholerae*, . The invention encompasses various compositions and methods for altering the expression of the subject genes with the aim of altering biofilm formation and thereby decreasing virulence and pathogenicity of *Vibrio*, species. Other embodiments provide methods and compositions for preventing the biofilm colonies from returning to a planktonic state, thus breaking the phenotypic cycle that allows release of *Vibrio*, into the environment. Specific embodiments of the invention are set out in the detailed description and in the claims.

DESCRIPTION OF THE TABLES AND FIGURES

Table 1, lists the plasmids and strains used in the study of rbmA.

Table 2, lists the bacterial strains and plasmids used in the study of rbmBCDEF and bap1.

Table 3, lists the primers used in the study of rbmBCDEF and bap1.

FIG. 1 Amino acid sequence of protein spot 1, corresponds to that of VC0928, . (A) Alignment of the 12-amino-acid sequence from protein spot 1, with a peptide sequence encoded by rbmA (locus VC0928), as obtained from TIGR. (B) The genetic organization of rbmA (open arrow) on the *V. Cholerae*, chromosome is depicted with locus annotations under each ORF. The vpsI and vpsII gene clusters, as well as the first and last genes of each cluster (vpsA and vpsK, vpsL and vpsQ) are marked and labeled. Unlinked chromosomal DNA regions within the vps clusters are also indicated (||) (C) The Genetic organization of the vps intergenic region. The genetic organization of rbmABCDEF and bap1, (open arrows) on the *V. cholerae*, chromosome is depicted with locus annotations under each open reading frame. The vpsI and vpsII gene clusters, as well as the first and last genes of each cluster (vpsA and vpsK, vpsL and vpsQ) are marked and labeled. Unlinked chromosomal DNA regions are indicated (||). Illustrations are not to scale.

FIG. 2 Bar graphs showing expression of the vpsA-lacZ and vpsL-lacZ fusion genes (carried in the pCC11, and pCC12, plasmids, respectively) in the wild type rugose and RΔrbmA variants grown in LB at 30° C. to mid-exponential growth phase (OD600=0.4). Error bars represent standard deviations. This data demonstrates that RbmA is critical to rugose colony formation and the expression of vpsA and vpsL is not altered in RΔrbmA.

Figure 3:
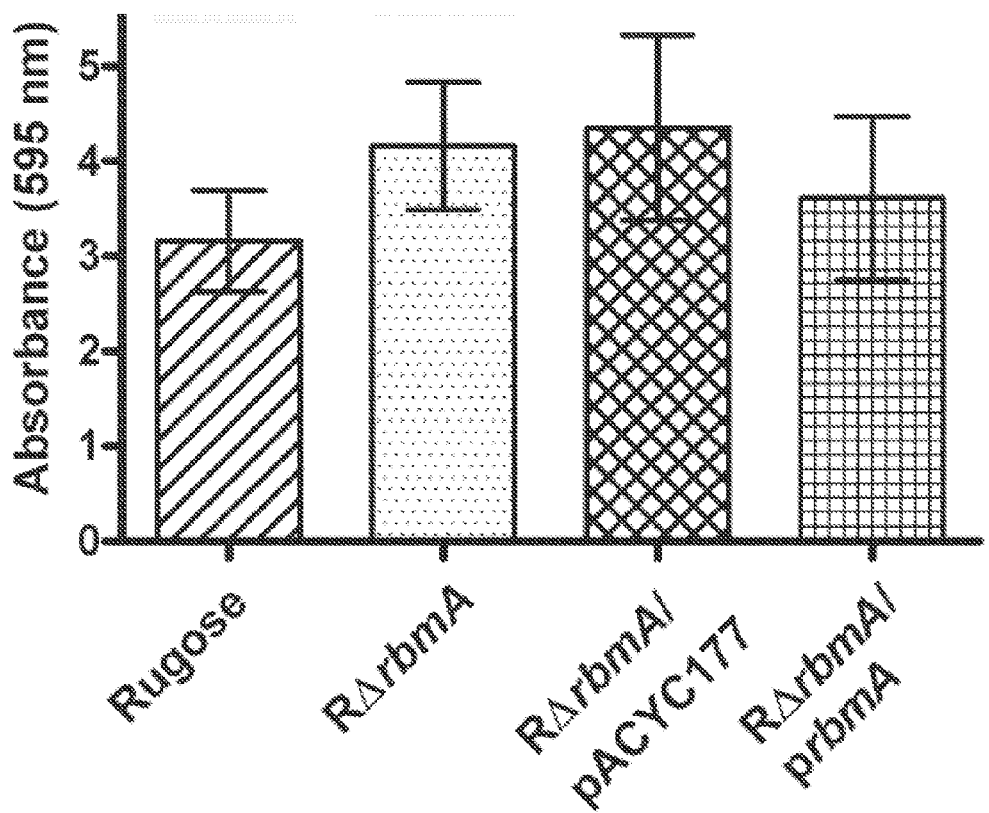

FIG. 3 The bar graph shows a quantitative comparison of biofilm formation by the wild type rugose variant, RΔrbmA, RΔrbmA/pACYC177, and RΔrbmA/prbmA, after an 8, h incubation in LB medium at 30° C. under static conditions. Error bars represent standard deviations. This data demonstrates that RbmA is required for biofilm structure.

Figure 4:
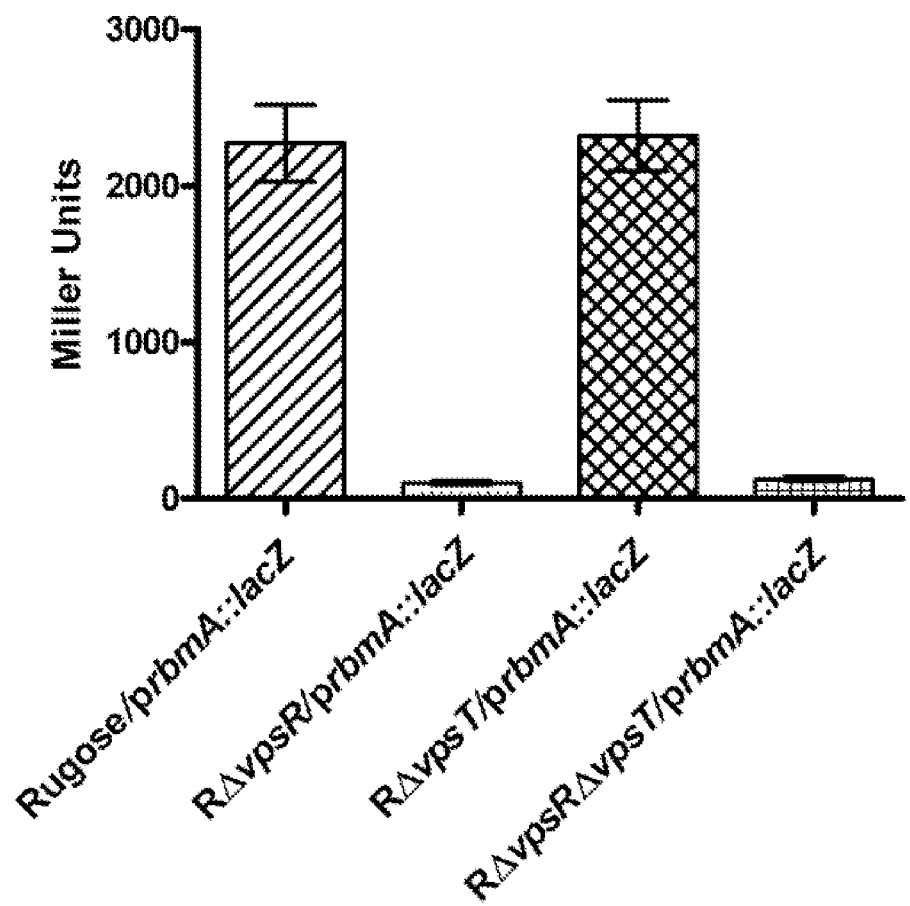

FIG. 4 The bar graph shows expression of a rbmA-lacZ fusion gene (prbmA::lacZ) in wild type, and in vpsR, vpsT and vpsRvpsT mutants of the rugose variant grown in LB at 30° C. to mid-exponential growth phase (OD600=0.4) is shown. Error bars represent standard deviations. This data demonstrates that VpsR is required for rbmA transcription.

FIG. 5 The bar graph shows quantitative analysis of biofilm formation by the rugose variant and RΔrbmB after 8, h of growth at 30° C. under static conditions. Error bars represent standard deviations. This data demonstrates that RbmB is required for rugose colony development and VPS accumulation.

FIG. 6 Bar graph showing expression of the vpsA::lacZ and vpsL::lacZ fusion genes in the rugose variant and RΔrbmB grown at 30° C. to mid-exponential growth phase. Error bars represent standard deviations.

FIG. 7 Bar graph showing quantitative comparison of biofilm formation by the rugose variant, RΔrbmC, RΔbap1, and RΔrbmCΔbap1, after 8, h of growth at 30° C. under static conditions. Error bars represent standard deviations. This data demonstrates that RbmC and Bap1 are involved in pellicle and biofilm formation.

FIG. 8 Bar graphs showing quantitative comparison of biofilm formation by the rugose variant, RΔrbmD, and RΔrbmEF after 8, h of growth at 30° C. under static conditions. Error bars represent standard deviations. This data demonstrates that rbmDEF deletion mutants are not significantly different in colony morphology and total biofilm formation compared to wild-type.

A number of colour photographs showing rugosity and biofilm formation for the strains and mutants employed in this study are available both in the original U.S. provisional patent applications (60/758,753, and 60/860,148) as well as in the related published scientific papers: Fong, J C and Yildiz, F. H. (2007) "The rbmBCDEF Gene Cluster Modulates Development of Rugose Colony Morphology and Biofilm Formation in *Vibrio cholerae*", accepted for publication in Journal of Bacteriology, January, 2007;, and Fong J C, Karplus K, Schoolnik G K, Yildiz F H. (2006) "Identification and characterization of RbmA, a novel protein required for the development of rugose colony morphology and biofilm structure in *Vibrio cholerae*", J Bacteriol. 188(3):1049-59, . Each of these applications and publications is herein incorporated by reference in its entirety to the fullest extent allowed for all purposes.

Description of the Sequence Listing: The content of the sequence listing information recorded in computer readable form is identical to the written (on paper or compact disc) sequence listing and includes no new matter.

DETAILED DESCRIPTION OF THE INVENTION

Definitions

In the present disclosure, when a particular gene or protein is referred to, the term is meant to encompass homologues and orthologues, variants, derivatives, and mutants of such a gene or protein. The present invention is not limited to embodiments employing the exact sequence of any of the Rmb proteins, polypeptides, polynucleotides etc, but encompasses any variant that is related by structure, sequence, function or is derived in any way from the named protein. For example, the present invention encompasses embodiments that include proteins or ligands that bind to RmbA and to any variant of RmbA having, for example, at least 30% primary amino acid sequence similarity to RmbA over a length of at least 100, amino acid residues, or in other embodiments, at least 40%, 50%, 75%, 90% or 99% primary protein sequence similarity to RmbA.

The terms "bind" and "binding" as used in this application encompasses a physical association of any type, including binding by covalent, ionic, or hydrogen bonds and by entropic forces.

The terms "interact" and "interacting" as used herein refer to any type of interaction between two species, whether or not a bond is present. Such an interaction may be permanent or transitory or of any intermediate quality.

The term "ligand" refers to any species, molecule or compound that may bind with or interact with another species, for example a ligand may be a protein or carbohydrate or an antibody or small molecule that interacts with a polynucleotide or enzyme. In the present application, for example, the binding of a ligand to a transcriptional regulatory protein may change the expression of a gene, or the binding of a ligand to a polynucleotide may result in a change in expression of the polynucleotide, or in other embodiments, the binding of a ligand to a enzyme may result in up-regulation or down-regulation of the activity of the enzyme. Those of skill in the art will readily recognize many scenarios in which a ligand may bind to another species to regulate expression or activity of an enzyme or other active molecule.

"Variants and analogues" of polynucleotides encompass polynucleotides that show structural similarity to the polynucleotide of which it is an analogue or variant. Structural similarity for polynucleotides refers to sequence similarity. A polynucleotide analogue may have, for example, at least 99%, 95%, 90%, 85%, 80%, 70%, 60%, 50%, or at least 40% similarity over the entire length of the original polynucleotide. Often variants that share functional motifs have a good deal less than 40% overall sequence similarity, and yet may still be reasonably described as variants or analogues. Alternatively it may have a similarity of at least 99%, 95%, 90%, 85%, 80%, 70%, 60%, 50%, or at least 40%, 30% or at least 20% similarity over a shorter length, for example over at least 1000, nucleotides, or at least 500, at least 250, at least 150, at least 100, at least 50, or at least 25, polynucleotides. Variants may be derivatives of the polynucleotide of which they are a variant, they may be chemically or biochemically modified and have one or more amino nucleotide substitutions, additions, and/or deletions. Variants may share certain functionally significant motifs with the polynucleotide of which they are a variant. These motifs may encode the portion of a protein that includes the active site of a protein, the portion that is essential to enzymatic activity. Sequence similarities and homologies may be reliably and consistently determined by using any of the well known Basic Local Alignment Search Tool (BLAST) software tools.

The term "mutant" when applied to a polynucleotide encompasses any polynucleotide similar to or derived from another polynucleotide that differs from the original polynucleotide by one or more additions, deletions or substitutions The term "delivery vehicle" encompasses any vehicle that aids in the delivery of a polynucleotide.

The term "vector" encompasses any delivery vehicle that biologically associates with a cell to deliver a polynucleotide, and includes, for example, a viral vector or a liposomal vector, and may also include naked DNA and RNA. An adenoviral vector includes any vector derived from an adenovirus, and a lentiviral vector includes any vector derived from a lentivirus.

Detailed Description of Various Embodiments

The invention encompasses compositions and methods relating to genes and proteins involved in colonization and pathogenesis of *Vibrio cholerae*, particularly rbmA, rbmB, rbmC, rbmD, rbmE, rbmF (in this disclosure this group of genes may be abbreviated as "rbmA, B, C, D, E, F") and Bapl and variants thereof. The invention relates to diagnostic, therapeutic, and environmental monitoring methods and devices and compositions, particularly for diagnosing, treating, and monitoring the presence of *Vibrio cholera*, and for reducing and preventing the formation of biofilm colonies. The invention encompasses various compositions and methods for altering the expression of the subject genes with the aim of altering biofilm formation and thereby decreasing virulence and pathogenicity of *Vibrio*, species. Other embodiments provide methods and compositions for preventing the biofilm colonies from returning to a planktonic state, thus breaking the phenotypic cycle that allows release of *Vibrio*, into the environment. Specific embodiments of the invention are set out in the detailed description and in the claims.

The invention includes methods and compositions for reducing colonisation and/or pathogenicity by altering the expression of one or more of rbmA, rbmB, rbmC, rbmD, rbmE, rbmF or Bapl or analogues or variants thereof, or by altering the activity of an enzyme encoded by one or more of these genes.

Specifically the invention encompasses the following embodiments:

A method for attenuating the virulence of a microbial pathogen or for inhibiting or reducing colonization by a microbial pathogen in a subject or on a surface, the method comprising administering to the subject or surface an effective amount of a ligand that binds to or interacts with the polynucleotides of rbmA, rbmB, rbmC, rbmD, rbmE, rbmF or Bapl or analogues or variants thereof, or to a protein encoded by such genes.

In some embodiments the ligand is an antibody that binds specifically to a protein encoded by rbmA, B, C, D, E, F or bap1, or analogues or variants thereof. In some pharmaceutical embodiments, the ligand may be any binding agent, and may, for example, include an antibody, or at least the Fab portion of an antibody. The agent may be formulated in a pharmaceutically acceptable formulation and administered orally so as to effectively and quickly reach the gastrointestinal tract. The agent may be delivered in a pharmaceutically acceptable delivery form, for example in a pill or capsule with an enteric coating to protect the agent against degradation by stomach acids.

In embodiments where the surface is an environmental surface, the agent may be formulated in a liquid or emulsion for administering to a surface by spraying or painting or other application method. In certain embodiments, the surface is a biological surface, for example a gastro-intestinal surface.

The invention additionally encompasses a method for attenuating the virulence of a microbial pathogen or for inhibiting or reducing colonization by a microbial pathogen in a subject or on a surface, the method comprising altering the expression of a polynucleotide of rbmA, B, C, D, E, F or bap1, or analogues or variants thereof.

In some embodiments, gene expression may be altered (reduced) by providing one or more species of small interfering RNA (siRNA) molecules to the subject or surface wherein the siRNA interfers with expression of rbmA, rbmB, rbmC, rbmD, rbmE, rbmF or bap1. The si RNA may be provided exogenously, for example by delivery via a vector, or may be produced endogenously, for example by the activity of an enzyme such as Dicer, an RNAse III ribonuclease that cleaves double-stranded RNA (dsRNA) and pre-microRNA (miRNA) into siRNA of about 20-25, nucleotides in length.

The invention additionally encompasses polynucleotides functionally linked to a constitutive or inducible promoter that controls the expression of the genes or operons of interest, such as rbmA, B, C, D, E, F or bap1. Such promoters may be of any known type that functions in the organism in question, for example promoters of the genes encoding ribosomal proteins or arabinose inducible pBAD promoters.

The present invention also encompasses the use of ligands and other species that regulate activity of the proteins and VPS lyase enzyme. Ligands that influence activity may include the sugars present in the exopolysaccharide of *Vibrio cholerae*, such as galactose, glucose, mannose and N-acetyl glucosamine. The present invention encompasses methods of regulating or altering the activity of VPS lyase enzyme and other proteins involved in colony formation of *V. cholerae*, by administering to a surface or culture or to a subject an amount of a sugar, for example, but not limited to, galactose, glucose, mannose and N-acetyl glucosamine. In practice, any ligand that binds to the lyase and competes with the natural sugar target may be employed. A ligand may be employed that binds with a very strong binding affinity, such that it occupies the enzyme and prevents it from binding to its natural carbohydrate target.

Additionally, it has been shown that proteins responsible for the turnover of a novel nucleotide, bis-(3'-5')-cyclic dimeric GMP (c-di-GMP), regulate the expression of vps genes and the genes located between the vps gene clusters (rbmA-F), in addition to the expression of the regulatory genes vpsR and vpsT. Both synthesis and degradation of c-di-GMP in the cell is modulated by proteins containing GGDEF and/or EAL domains, which function as a diguanylate cyclase and a phosphodiesterase, respectively. The present invention includes the use of such regulatory proteins to regulate the expression of vps genes and operons by administering to a surface or culture or to a subject an amount of a protein described above.

The invention additionally encompasses a method for attenuating the virulence of a microbial pathogen or for inhibiting or reducing colonization by a microbial pathogen in a subject or on a surface, the method comprising administering to subject or surface a ligand that alters the expression of a polynucleotide of rbmA, B, C, D, E, F or bap1, or analogues or variants thereof, or that alters the activity of a polypeptide (such as an enzyme) encoded by such genes.

Such methods may comprise administering to the subject or surface an effective amount of a ligand that binds to or interacts with a polynucleotide of rbmA, B, C, D, E, F or bap1, or analogues or variants thereof.

In this disclosure, altering the activity of a polypeptide includes altering its enzymatic activity or binding affinity. The polypeptide in question may bind to another protein, for example as an allosteric binding protein altering the activity of an enzyme, or to a polynucleotide altering expression.

The present invention also encompasses a method for attenuating the virulence of a microbial pathogen or for inhibiting or reducing colonization by a microbial pathogen in a subject or on a surface, the method comprising administering to a subject a gene selected from the group consisting of rbmA, B, C, D, E, F or bap1, or variant thereof.

The invention also includes a method for attenuating the virulence of a microbial pathogen or for inhibiting or reducing colonization by a microbial pathogen in a subject or on a surface, the method comprising administering to a subject a vector, e.g., an adenoviral vector, comprising a gene selected from the group consisting of rbmA, B, C, D, E, F or bap1, or variant thereof.

A method for preventing, reducing or attenuating biofilm formation of *Vibrio cholerae*, on a surface e.g., a gastrointestinal surface), the method comprising contacting to the *Vibrio cholerae* an agent that interacts with rbmA, B, C, D, E, F or bap1, or variant thereof, or with a protein encoded thereby.

A pharmaceutical composition comprising an agent that binds to or interacts with a polynucleotide selected from rbmA, B, C, D, E, F or bap1, or variant thereof.

A method for treating a subject infected with *Vibrio cholerae*, the method comprising administering to the subject a therapeutically effective amount of a composition or agent above or by practicing one of the above methods upon the subject.

A diagnostic kit comprising an agent that binds to or interacts with a polynucleotide selected from the group consisting of rbmA, B, C, D, E, F or bap1, or variant thereof or to a protein encoded by such a polynucleotide.

A method for diagnosing an infection by *Vibrio cholerae*, the method comprising providing a subject, taking a biological sample from said subject, and contacting said biological sample with an agent that binds to or interacts with a polynucleotide selected from the group consisting of rbmA, B, C, D, E, F or bap1, or variant thereof or to a protein encoded by such a polynucleotide.

An assay kit for detecting the presence of *Vibrio cholerae*, the kit comprising an agent that binds to or interacts with a polynucleotide selected from the group consisting of rbmA, B, C, D, E, F or bap1, or variant thereof or to a protein encoded by such a polynucleotide.

A method for detecting the presence of *Vibrio cholerae*, in an environment, the method comprising contacting said environment with an agent that binds to or interacts with a polynucleotide selected from the group consisting of rbmA, B, C, D, E, F or bap1, or variant thereof or to a protein encoded by such a polynucleotide.

Such a method may be qualitative or quantitative. Such a method may include amplification of the polynucleotide by PCR. Such methods and assays are typically performed using specific antibodies that bind to a target molecule, and the present methods may be performed, for example using standard ELISA assay techniques. The method of detection may be quantitative to allow detection of an organism in an environment to monitor the population of the organism, and thereby monitor and predict outbreaks.

The invention also includes a polynucleotide delivery system comprising a delivery vehicle and a polynucleotide selected from the group consisting of rbmA, B, C, D, E, F or bap1, or variant thereof. The delivery vehicle may be, for example, a liposome or a viral delivery vehicle such as an adenoviral vector or lentiviral vector or vector derived from either of these types of virus or from another virus.

EXAMPLE 1

Investigation of RbmA

A complete description of this study is found in the publication: Fong J C, Karplus K, Schoolnik G K, Yildiz F H. (2006) "Identification and characterization of RbmA, a novel protein required for the development of rugose colony morphology and biofilm structure in *Vibrio cholerae*", J Bacteriol. 188(3):1049-59, which is herein incorporated by reference in its entirety to the fullest extent allowed for all purposes. Changes in the proteome that accompanies the smooth to rugose phase variation were investigated using two-dimensional gel electrophoresis on whole cell extracts of exponential- and stationary-phase grown *V. cholerae*, cultures. The inventor identified a protein (RbmA) that is produced at higher level in the rugose variant. Using mutational analysis, the inventors determined that RbmA is required for the full development of corrugated rugose colonial morphology and of "typical" pillar structures of biofilms. In addition, the inventors established that RbmA production is regulated by VpsR.

Phase variation between smooth and rugose colony variants of *Vibrio cholerae*, is predicted to be important for the pathogen's survival. The rugose variant forms corrugated colonies, exhibits increased levels of resistance to osmotic, acid and oxidative stresses, and has an enhanced capacity to form biofilms. Many of these phenotypes are mediated in part by increased production of an exopolysaccharide termed VPS. In this study, the inventors compared total protein profiles of the smooth and rugose variants using two-dimensional gel electrophoresis and identified one protein (RbmA) that is present at a higher level in the rugose variant. RbmA does not have any known homolog in the protein databases. A strain containing a mutation in the rbmA gene forms biofilms that are more fragile and sensitive to SDS than wild type biofilms. The results indicate that the rbmA (rugosity and biofilm structure modulator A) is required for rugose colony formation and biofilm structure integrity in *V. cholerae*, . Transcription of rbmA is positively regulated by the response regulator VpsR but not VpsT.

Materials and Methods Used for Investigation of RbmA

Bacterial strains, plasmids, and culture conditions. The bacterial strains and plasmids used in this study are listed in Table 1, . All *V. cholerae*, and *Escherichia coli*, strains were routinely grown aerobically, in Luria-Bertani (LB) medium, at 30° C. and 37° C., respectively, unless otherwise noted. Agar medium contained 1.5% (wt/vol) granulated agar (Difco), except for motility studies, where the agar concentration was 0.3% (wt/vol). Concentrations of antibiotics used were as follow: ampicillin (100, μg/ml), rifampicin (100, μg/ml) and gentamicin (30, μg/ml). Pellicle formation experiments were carried out in glass culture tubes (18×150, mm) containing 5, ml of LB medium or LB medium supplemented with ampicillin, inoculated with 200-fold diluted overnight-grown cultures. The tubes were incubated at 30° C. under static conditions for 2, days. Cultures grown for colony morphology observations were also incubated at 30° C. for 2, days.

Recombinant DNA techniques. DNA manipulations were carried out by standard molecular techniques. Restriction enzymes and DNA modification enzymes were obtained from New England Biolabs. Polymerase chain reactions (PCR) were carried out using primers purchased from Operon Technologies and the High-Fidelity PCR kit (Roche).

Two-dimensional (2D) SDS-PAGE. Rugose and smooth *V. cholerae*, wild type cells were harvested during exponential and stationary growth phases and resuspended in 125-250, μl of lysis buffer containing 0.3% SDS, 10, mM Tris (pH 7.4), 100, μg/ml deoxyribonuclease I (DNase I Type II from bovine pancreas) and 50, μg/ml ribonuclease A (RNase A Type IIIA from bovine pancreas) in 5, mM $MgCl_2$, and 10, mM Tris-Cl (pH 7.0), and 1% protease inhibitor stock [20, mM 4-(2-aminoethyl)benzenesulfonyl fluoride hydrochloride (AEBSF), 1, mg/ml leupeptin, 0.36 mg/ml E-64, 500, mM ethylenediaminetetraacetic acid (EDTA) and 5.6, mg/ml benzamidine]. The cells were then vortexed and incubated on ice for 5, min. An equal volume of SDS boiling buffer, composed of 5% SDS, 10% glycerol and 60, mM Tris (pH 6.8), was added and protein concentrations were determined using the BCA assay (Pierce). Before loading the samples for SDS-polyacrylamide gel electrophoresis (PAGE), β-mercaptoethanol was added to a final concentration of 5% (vol/vol). Labeling of exponentially-grown cultures (1, ml) was carried out with 40, μCi of [$^{35}$S] methionine (Du Pont NEN, Wilmington, Del.) for 3, min followed by a 1-min chase with 0.2, mM unlabeled methionine. Labeling time was increased to 15, min for stationary-phase cultures, followed by a 5-min chase with unlabeled methionine. The samples were washed twice with phosphate-buffered saline (PBS). The amount of [$^{35}$S] methionine incorporated was determined by liquid scintillation counting of a small portion of the cell lysate precipitated with 10% trichloroacetic acid (TCA). Protein samples were loaded at 2,200,000 cpm and 2D gel electrophoresis was carried out with a Protean II (Bio-Rad) device as described by the manufacturer. Labeled proteins were visualized by autoradiography. The following $^{14}$C molecular weight markers (Amersham) were added to a well in the agarose that sealed the tube gel to the slab gel: myosin (220, kDa), phosphorylase B (97, kDa), bovine serum albumin (66 kDa), ovalbumin (45, kDa), carbonic anhydrase (30, kDa) and lysozyme (14, kDa). These markers appeared as faint bands at the basic end of the x-ray films. For Coomassie blue-stained gels, 250 µg of each protein sample were loaded. The following proteins (Sigma) were added as molecular weight standards to a well in the agarose that sealed the tube gel to the slab gel: myosin (220, kDa), phosphorylase A (94, kDa), catalase (60, kDa), actin (43, kDa), carbonic anhydrase (29, kDa) and lysozyme (14, kDa). These standards appear as horizontal lines on the Coomassie brilliant blue R-250-stained, 10% acrylamide slab gels. 2D protein electrophoresis was conducted according to the method of O'Farrell by Kendrick labs, Inc. (Madison, Wis.). Briefly, isoelectric focusing (JEF) was carried out in glass tubes with an inner diameter of 2.0 mm, using 2.0%, pH 4-8, ampholines (BDH from Hoefer Scientific Instruments) at 9600, volt-h. One microgram of an IEF internal standard, tropomyosin protein, with a molecular weight of 33 kDa and pI 5.2, was added to the samples. The positions of the standard are indicated by arrowheads on the stained 2D gels. After equilibration for 10, min in Buffer O (10% glycerol, 50 mM dithiothreitol, 2.3% SDS and 0.0625, M Tris, pH 6.8) the tube gels were sealed to the top of the stacking gels, which were above the 10% acrylamide slab gels (0.75, mm thick). SDS slab gel electrophoresis was carried out for about 4, hrs at 12.5, mA/gel. Protein spot 1, was excised from the Coomassie blue-stained gels and subjected to enzymatic digestion and internal sequencing. Following 2D SDS-PAGE analysis on two different biological replicates, proteins differentially produced in rugose and smooth cells were identified visually.

Generation of in-frame rbmA deletion mutants in smooth and rugose variants of *V. cholerae*, . The 5' (560, bp) and 3' (417, bp) regions of the rbmA gene, which encodes VC0928, were amplified by PCR with primers VC0928_, del_, A (GATCTCTAGACTGTTTGTGGCGATCACATC) (SEQ ID NO: 1) and VC0928_, del_, B (CAGAAACAATACAACTGGCGCTAAGGCTAA) (SEQ ID NO: 2), and primers VC0928_, del_, C (CGCCAGTTGTATTGTTTCTGGTGAGCGAGT) (SEQ ID NO: 3) and VC0928_, del_, D (GATCCCATGGTCGTTTCTTTCGAACATGTCA) (SEQ ID NO: 4), respectively. The two PCR products generated (termed AB and CD) were then joined via SOEing (splicing by overlap extension) PCR with primers VC0928_, del_, A and VC0928_, del_, D. Overlapping nucleotide sequences (20, bp) were incorporated into primers VC0928_, del_, B and VC0928_, del_, C to facilitate SOEing PCR. The amplified, 997-bp deletion fragment was cloned into pGP704-sacB28, via nal and NcoI restriction enzyme sites, which were incorporated into primers VC0928_, del_, A and VC0928_, del_, D, respectively.

The accuracy of the deletion fragment was verified by DNA sequencing. The deletion recombinant plasmid (pGPVC0928) was used to transform the cloning strain *E. coli*, CC118, (λ pir), purified and then used to transform the conjugative strain *E. coli*, S17-1, (λ pir). S17-1, (λ pir) was then conjugated with *V. cholerae*, smooth and rugose variants separately. Transconjugants were selected on LB agar medium containing 100, μg/ml of ampicillin and rifampicin. Sucrose-based selection was used to select *V. cholerae*, deletion clones that had undergone homologous recombination between the wild type chromosomal copy of rbmA and the 997-bp deletion fragment. Briefly, 16, independent ampicillin and rifampicin resistant transconjugants were randomly selected and streaked on LB agar plates containing 100, μg/ml of ampicillin and rifampicin, and incubated at 37° C. Single colonies were then streaked on LB agar plates containing 100, μg/ml of ampicillin and 6% (wt/vol) sucrose without NaCl, or 100, μg/ml of ampicillin alone, to test for sucrose sensitivity and ampicillin resistance. Culture plates were incubated at 37° C., except for those containing sucrose, which were incubated at room temperature. Six ampicillin resistant and sucrose sensitive clones were selected and inoculated into 5, ml of LB medium and incubated at 37° C., with shaking at 200, rpm for 6, h. A loopful (1 μl) of the 6-h grown liquid culture was then streaked on LB agar plates containing 6% (wt/vol) sucrose without NaCl and incubated at room temperature for 2, days. Deletion mutants growing on the sucrose-based medium were selected, streaked for single colonies on LB agar medium. Presence of the deletion was verified by PCR. Deletion mutants of rbmA generated in smooth and rugose backgrounds were designated as SΔArbmA and RΔrbmA, respectively.

Generation of complementation strains in RΔrbmA. The complementation plasmid prbmA was constructed by cloning an amplified 1,113-bp fragment of rbmA (including 174, by upstream to 123, by downstream of the predicted rbmA ORF), using primers VC0928_, com F (GATCAAGCTTtttggtttattttgetttctgg) (SEQ ID NO: 5) and VC0928_, com R (GATCCTCGAGtgaggaaageggtaaactcc) (SEQ ID NO: 6), into pACYC 177, via HindIII and XhoI sites, which were incorporated into the primers. Following electroporation of prbmA into electro-competent RΔrbmA cells, complemented clones were selected on LB agar medium containing ampicillin (100, μg/ml).

Generation of RΔrbmA expressing Myc-tagged RbmA. The 813, by coding region of rbmA (including the start codon but excluding the stop codon) was amplified with primers VC0928myc F (GATCCTCGAGGTTGTCTAACTTTAAAGGATCTATCA) (SEQ ED NO: 7) and VC0928myc R (GATCTCTAGATTTTTTTTTACCACTGTCATTGACTG) (SEQ ID NO: 8) and directionally cloned into plasmid pBAD/Myc-His B (Invitrogen) via XhoI and XbaI sites, in-frame with the downstream Myc epitope and six histidine codons. The resulting C-terminal Myc-tagged expression vector prbmA-myc was electroporated into electro-competent RΔrbmA cells and recombinant clones were selected on LB agar medium containing ampicillin (100 μg/ml).

Generation of rbmA-lacZ fusion strains in *V. cholerae*, rugose variant. A 292-bp DNA fragment immediately upstream of the predicted rbmA ORF was amplified with primers P0928 F1, (GATCGAATTCGTTACAAGAACCCGGAAGAATG) (SEQ ID NO: 9) and P0928, R1 (GATCGGATCCCCATTTGTTTTTACAACTGGCGCTAA) (SEQ ID NO: 10). The amplified product was cloned into the promoterless lacZ vector pRS415, via EcoRI and BamHI sites, generating the rbmA-lacZ fusion construct prbmA::lacZ, which was used to transform *E. coli* DH5α. In constructing *V. cholerae*, rbmA-lacZ fusion strains, prbmA::lacZ was electroporated into electrocompetent rugose *V. cholerae*, strains harboring a lacZ deletion (RugoseΔlacZ); vpsT and lacZ deletions (RΔvpsT ΔlacZ); vpsR and lacZ deletions (RΔvpsR ΔlacZ); and vpsR, vpsT and lacZ deletions (RΔvpsR ΔvpsT ΔlacZ). Recombinant clones were selected on LB agar medium containing 100, μg/ml ampicillin.

β-Galactosidase assays. β-galactosidase activity was determined. Briefly, overnight cultures of *V. cholerae*, were diluted 200-fold and inoculated into fresh LB medium. Cells in the exponential growth phase were harvested when $OD_{600}$, reached 0.4, . Different dilutions of 100, μl of cell culture were pipetted into wells of a MultiScreen&HA 96-well microtiter plate fitted onto a MultiScreen® filtration system (Millipore). Culture medium was removed by applying a vacuum to the filtration system. The cells were then washed with 200, μl of Buffer Z (16.1, g/l $Na_2HPO_4.7H_2O$, 5.5, g/l $NaH_2PO_4.H_2O$, 0.75, g/l KCl, 0.246, g/l $MgSO_4.7H_2O$) at pH 7.0.

Cell lysis was carried out by adding 100, μl of Buffer Z containing 0.69% (vol/vol) β-mercaptoethanol, 0.02% (wt/vol) cetyltrimethyl ammonium bromide (C-TAB) and 0.01% (wt/vol) deoxycholic acid sodium salt (Na-DOC), followed by incubation at room temperature for 5, min. ONPG solution (20, μl of 4, mg/ml) was added to the lysed cell suspensions and these were further incubated at 30° C. until sufficient color development was observed. The duration of color development was noted for each culture. The reaction was stopped by adding 50, μl of 1, M $Na_2CO_3$. The intensities of color were measured at OD 420, nm and 550, nm, after transferring the samples to a new flat-bottom 96-well microtiter plate. Miller units for β-galactosidase activity were calculated using the formula: Miller Units=$1000\times(OD_{420}-1.75\times OD_{550})/(t\times v\times OD_{600})$, where t is the reaction time in minutes and v is the assay volume in milliliters. The data were presented as average values of at least 3, technical replicates from one representative experiment, which was repeated 3, times with different biological replicates showing similar data.

Quantitative biofilm assays. Biofilm formation assays were carried out in polyvinyl chloride microtiter plates following a method previously described. Briefly, 100, μl of 200-fold diluted overnight cultures were pipetted into the wells of 96-well microtiter plates. The plates were incubated at 30° C. for 8, h. Liquid medium in each well was discarded, and the plates were washed once gently with water. Crystal violet staining and ethanol solubilization were carried out, as previously described, to quantify biofilm formation. The data were presented as average values of at least 15, technical replicates from one representative experiment, which has been repeated 3, times with different biological replicates showing similar data.

Generation of GFP-tagged strains of *V. cholerae*, wild type variants and rbmA deletion mutants. GFP-tagged wild-type rugose and rbmA deletion mutant were generated by triparental conjugation with donor *E. coli*, S17-1, (λ pir) carrying pGP707::Tn7-GFP (a mini-Tn7 transposon containing the gfpmut3, gene under the control of a constitutive ribosomal promoter) and helper *E. coli*, S17-1, (λ pir) harboring pUX-BF13, containing the Tn7, transposase gene. The mini-Tn7, transposon targets the chromosomal region between loci VC0487, and VC0488. Transconjugants were selected on TCBS (Difco) agar medium containing 30, μg/ml gentamicin at 30° C. GFP-tagged strains were verified by PCR analysis and fluorescence microscopy.

Flow cells and confocal scanning laser microscopy (CSLM). Overnight cultures, grown in LB liquid medium at 30° C. with shaking at 200, rpm, were diluted to $OD_{600}$=0.02, and 200, μl aliquots were inoculated by injection into flow cell chambers. Before inoculation, the chambers were sterilized and equilibrated with 1, liter of 0.5% (vol/vol) hypochlorite, followed by 1, liter of sterile MilliQ water and 200, ml of 2% LB (0.2, g/l tryptone, 0.1, g/l yeast extract, 9, g/l NaCl) at a flow rate of 0.26, ml/min.

After inoculation, the chambers were allowed to stand inverted, with no flow, for 1, h. Flow was resumed at a rate of 0.26, ml/min with chambers standing upright for 30, min. Flow cell experiments were carried out at room temperature. Confocal images of biofilms that formed in flow cell chambers were captured with a LSM 5, PASCAL system (Zeiss) at 488, nm excitation and 543, nm emission wavelengths. Three dimensional images of the biofilms were reconstructed using Imaris® software (Bitplane) and quantified using COMSTAT®. For the biofilm structure integrity studies, 0.2% (wt/vol) SDS was used.

Cellular Fractionation. Overnight cultures were diluted 100-fold and inoculated into fresh LB medium containing ampicillin. Cells in the exponential growth phase ($OD_{600}$=0.3) were then induced with 0.1% (wt/vol) arabinose for 1, h. Cultures (30, ml) were harvested by centrifugation (10,000×g) and cellular fractionation was carried out. Briefly, the cell pellet was resuspended in PBS containing polymyxin B sulfate (10,000, units) and incubated on ice for 10, min. The soluble periplasmic fraction was collected after centrifugation (10,000×g) at 4° C. for 10, min. The spheroplast pellet was resuspended in 10, mM Tris-Cl (pH 8.0) and cells were lysed by sonication (10, sec pulses repeated 5, times). Unlysed cells were removed by repeated centrifugations (10,000×g) at 4° C. for 15, min each. The soluble cytoplasmic fraction was separated from total membranes by centrifugation of the lysate (100,000×g) at 4° C. for 1, h. The inner and outer membranes were differentially solubilized by resuspending the total membrane pellet in 10, mM Tris-Cl containing 100, mM NaCl and 2.5% (wt/vol) Sarkosyl, and incubated at room temperature with shaking for 30, min. The soluble inner membrane fraction was separated from the outer membrane pellet by centrifugation at 200,000×g at 4° C. for 1, h. The outer membrane was resuspended in 200, μl of 10, mM Tris-Cl (pH 8.0).

Proteins in the culture supernatant were precipitated using TCA. Briefly, 2, ml of 0.15% (wt/vol) Na-DOC was added to 20, ml of culture supernatant, vortexed, and incubated at room temperature for 10, min. Then, 2, ml TCA were added, and the samples vortexed and incubated on ice for 30, min. The protein precipitate was pelleted by centrifugation at 10,000×g for 10 min at 4° C. The pellet was washed twice with ice-cold acetone and resuspended in 200, μl of 10 mM Tris-Cl (pH 8.0). Protein concentrations were estimated using a BCA protein assay kit (Pierce) with bovine serum albumin as standard. Protein samples were loaded at 5, and 1, μg for immunoblot analysis of RbmA and OmpU, respectively.

Immunoblot analysis. Proteins from various cellular and culture supernatant fractions were separated on a 10% SDS polyacrylamide gel and electroblotted onto a nitrocellulose membrane with a Mini Trans-Blot Cell (Bio-Rad) apparatus in transfer buffer containing 25, mM Tris (pH 8.3), 192, mM glycine, 20% (vol/vol) methanol and 0.1% (wt/vol) SDS. The blot was blocked with 2% (wt/vol) skim milk and washed with PBS buffer containing 250, mM NaCl and 0.1% (vol/vol) Tween 20, . Rabbit polyclonal antisera against *V. cholerae*, OmpU (provided by K. Klose) was used at a dilution of 1:100,000, while mouse monoclonal antibody against the Myc epitope (Santa Cruz Biotechnology) was used at a dilution of 1:1,000, . Horseradish peroxidase-conjugated goat anti-rabbit and anti-mouse secondary antibodies (Santa Cruz Biotechnology) were used at a dilution of 1:2,500, . Immunoblots were developed with the SuperSignal West Pico chemiluminescent kit (Pierce). Immunoblot analyses were conducted using two biological replicates and two technical replicates.

Results of Investigation of RbmA

The protein profiles of the rugose and smooth variants are different. To identify changes in total protein production patterns resulting from phase variation, smooth and rugose cultures were labeled with [$^{35}$S] methionine during both exponential and stationary phases of growth and labeled proteins were then identified by 2D gel electrophoresis. Results of such analyses, which are provided as a supplementary data, show differences in total-protein profiles between the two variants, whereby phase variation negatively and positively regulates productions of multiple proteins.

To determine the identity of the proteins that are differentially produced, crude protein extracts from whole cell lysates were separated by 2D-gel electrophoresis and the gels were stained with Coomassie blue. Analysis of the proteins produced by smooth and rugose variants during exponential and stationary growth phases revealed that at least four protein spots were differentially produced. Protein spot 1, was produced at higher levels in cell lysates from the rugose variant compared to those from the smooth one. Similarly, protein spots 2, and 3, were present in higher amount in crude protein extract from the exponentially grown rugose variant. Protein spot 4, was present in lower amount in lysates from the rugose variant grown to stationary phase. In addition, two other protein spots appear to be present in slightly higher amounts in the protein sample from stationary-phase grown rugose variant compared to the smooth one (these gels are shown in figures in Fong J C, Karplus K, Schoolnik G K, Yildiz F H. (2006) "Identification and characterization of RbmA, a novel protein required for the development of rugose colony morphology and biofilm structure in *Vibrio cholerae*", J Bacteriol. 188(3):1049-59).

The inventors focused their studies on protein spot 1, and determined the sequence of 12, amino acids (SEQ ID NO: 47) corresponding to the internal part of the protein, which aligned to the amino acid sequence of the hypothetical protein annotated as VC0928, (SEQ ID NO: 48) in the *V. cholerae*, E1, Tor N16961, genome (FIG. 2A). The inventors named the gene locus VC0928, rbmA (for rugosity and biofilm structure modulator A) (SEQ ID NO: 49), because of evidence that it is involved in rugose colony and biofilm structure formation (discussed below). There are two possible start codons encoding methionine (M1, and M9) in rbmA (FIG. 2A). Blast searches of the non-redundant protein database (NCBI) using the predicted polypeptide sequences beginning with either methionine did not reveal any significant homologs, suggesting that this protein may only be present in *V. cholerae*, . The closest hit had an E-value of 0.19, for a *Mesorhizobium loti* sequence of unknown function. More sensitive searches using the Sequence Alignment and Modeling Software System (SAM-T2K and SAM-T04, methods) were also unsuccessful in finding any similar sequences. Using the TMHMM (transmembrane helices prediction), SignalP (signal peptide cleavage sites prediction), and LipoP (lipoproteins and signal peptides prediction) programs, a strong prediction was given for a signal peptide with cleavage between A30, and E31 (probability 0.922, and 0.998, for the two SignalP methods). The inventors next attempted to understand the function of this protein using structure prediction programs; their outputs are presented in discussion section.

The rbmA gene is located in the vps region between the vpsI and vpsII clusters (FIG. 1), which contain the genes required for VPS production. Putative regulatory elements (−10, and −35 regions and terminator sequences) have been predicted up- and down-stream of the rbmA ORF, suggesting that it is expressed as a monocistronic transcript and not part of an operon structure. Immediately upstream of rbmA is the last gene of the vpsI cluster (vpsK, VC0927) predicted to encode a UDP-N-acetyl-D-mannosamine transferase. Directly downstream of rbmA is the locus VC0929, predicted to encode for a hypothetical protein 408, amino acids in length and then several ORFs predicted to encode for a hemolysin-related protein (VC0930), 3, hypothetical proteins (VC0931-3) and the first gene of the vpsII cluster (vpsL, VC0934), which encodes a capsular polysaccharide biosynthesis glycosyltransferase. Inactivation of locus VC0930, using transposon TnphoA insertion resulted in a switch from rugose to smooth colonial phenotype, suggesting that the genes located between the two vps clusters play a role in maintaining rugose colony formation in *V. cholerae*.

Deletion of rbmA affects rugose colonial morphology. The close proximity of rbmA to the vps clusters prompted us to ask whether the gene is involved in cellular processes that are affected by the expression of vps genes. To identify the function of rbmA, deletion mutants were generated in both the rugose (RΔrbmA) and smooth (SΔrbmA) variants. Deletion of rbmA in the rugose variant decreased the corrugation of rugose colonies, but did not lead to completely smooth colony formation.

Complementation of RΔrbmA using the plasmid prbmA, which harbors the wild type copy of rbmA (including 174, by up- and 123, by down-stream from the predicted ORF) on a low-copy number vector, restored the normal rugose colonial morphology. In contrast, RΔrbmA transformed with plasmid vector alone retained its abnormal colonial morphology. No obvious differences in colonial morphology were observed in the rbmA deletion mutant generated in the smooth variant, when compared to wild type. Together, these results show that RbmA is required for rugose colony formation in *V. cholerae*.

The inventors also determined the abundance of transcripts corresponding to the vpsA and vpsL genes in RΔrbmA to investigate whether expressions of these two genes, known to be important to rugose colonial morphology, was altered. To this end, vpsA- and vpsL-lacZ fusion plasmids (pCC11, and pCC12, respectively) were introduced into the,wild-type rugose variant and RΔrbmA and β-galactosidase activities were determined. There are no significant differences in transcriptional abundance of vpsA and vpsL, between wild type and RΔrbmA. Both wild type and RΔrbmA rugose variants containing vector alone showed negligible background β-galactosidase activities (data not shown). These results demonstrate that vps genes expression is not altered in RΔrbmA and therefore, the less-corrugated colonial morphology of RΔrbmA is due to the loss of RbmA function.

rbmA is critical for biofilm structure and fitness. The biofilm forming capacity of the rugose variant is greatly enhanced compared to that of the smooth variant. Since RΔrbmA exhibited an altered colonial morphology, the inventors asked whether the biofilm-forming property of RΔrbmA was also altered relative to wild type. Thus, the inventors first compared the biofilm-forming properties of the two strains by crystal violet staining of biofilms formed on microtiter plates after 8, h incubation under static conditions at 30° C. The results, shown in FIG. 3, revealed that the biofilm-forming capacity of RΔrbmA was not significantly different from that of the wild-type rugose variant. This finding suggests that rbmA has a different role than the genes that encode for VPS biosynthesis, since vps mutants have reduced biofilm-forming capacities. The rugose variant also forms a pellicle which is a biofilm formed at air-liquid interface. When cultures are grown statically, RΔrbmA forms a pellicle that appears slightly less-developed (that is, less-wrinkled) compared to that of the rugose variant. Upon shaking, the pellicle formed by RΔrbmA broke into pieces, suggesting that it might have been more fragile. In contrast, the pellicle formed by the wild-type rugose variant detached as an aggregate. Differences in the stability of pellicles prompted us to find structural differences between the biofilms formed by RΔrbmA and wild-type rugose variant.

To understand the dynamics of biofilm development in a flowing system, the inventors first analyzed biofilm formation by confocal scanning laser microscopy (CSLM) as a function of time using a once-through flow cell reactor and green fluorescent protein (GFP)-tagged strains. After 12, h, the biofilm formed by RΔrbmA appears less-developed (that is, less-differentiated) compared to that of the wild type rugose variant. COMSTAT analysis of the biofilms revealed that the RΔrbmA biofilm is thicker in height (average thickness of 61, µm compared to 14, µm for the wild type), less organized, and more disperse (that is, loosely packed). These differences were more evident after 48, h, when the average thickness of the rugose biofilm was 200, µm compared to 312, µm for RΔrbmA. The increased thickness of the biofilm structure of RΔrbmA is not likely to be due to an increase in VPS production, since vpsA and vpsL gene expression and total biofilm mass (as determined by crystal violet quantification) are similar between RΔrbmA and wild type. Treatment of biofilms with 0.2% (wt/vol) SDS for 5, min destroyed the biofilm formed by RΔrbmA and after 20, min of SDS treatment the biofilm had almost completely detached. On the other hand, the biofilm formed by the rugose variant remained relatively intact after the same treatment. The differences observed in pellicle and biofilm formation could not be attributed to an altered growth rate of the mutant, since there was no difference in the growth rate of RΔrbmA compared to wild type. Together, these results show that RbmA is required for the formation of structurally mature biofilms and for biofilm fitness in V. cholerae.

RbmA is a secreted protein. To investigate the cellular localization of RbmA, a chimeric protein was generated by translational fusion of the C-terminus of RbmA to a Myc epitope and six histidine residues (in pBAD/Myc-His B). Transcription of the fusion protein was under the control of an arabinose inducible promoter. Exponentially grown RΔrbmA, harboring the translational fusion plasmid prbmA-myc, was induced with 0.1% (wt/vol) arabinose, harvested, and fractionated into cellular components. Anti-Myc antibody (α-Myc) detected an immunoreactive polypeptide of approximately 31, kDa in the TCA precipitated culture supematant (CS) fraction. In contrast, such a band was not detected in the uninduced CS fraction, or in both induced and uninduced periplasmic, inner membrane (IM) and outer membrane (OM) fractions (data not shown). A faint band of 31, kDa was also detected in the induced (but not in the uninduced) cytoplasmic fraction. As a control, immunoblot analysis of cellular fractions and TCA precipitated CS fractions was also carried out with anti-OmpU antisera (α-OmpU). A strong signal corresponding to an immunoreactive polypeptide of the expected size for OmpU in V. cholerae, was detected in the OM fractions from both induced and uninduced cultures. Together, these results indicate that RbmA is predominantly present in the culture supernatant fraction of V. cholerae, and, thus, likely to be a secreted protein.

Expression of rbmA is regulated by VpsR. The response regulators VpsR and VpsT regulate the expression of vps genes and the formation of corrugated colonies. To study a possible effect of VpsR and VpsT on the expression of rbmA, a rbmA-lacZ transcriptional fusion (prbmA::lacZ) plasmid was constructed and electroporated into wild type rugose, RΔvpsR, RΔvpsT, and RΔvpsR ΔvpsT strains. The chromosomal copy of lacZ in these strains has been inactivated by an in-frame deletion to prevent background β-galactosidase activity. High levels of β-galactosidase activity were detected in the wild type rugose and RΔvpsT strains harboring prbmA::lacZ, but not in RΔvpsR (β-galactosidase activity was 17-fold lower than in wild type) or R×vpsR ×vpsT (14-fold lower than wild type) (FIG. 4). All strains carrying the vector pRS415 showed negligible background β-galactosidase activity (data not shown). These results indicate that expression of rbmA is positively regulated by VpsR. Thus, rbmA is likely to be coordinately expressed with the vps genes.

Discussion of RbmA Results

Phase variation between smooth and rugose variants-is believed to be linked to the survival of V. cholerae, . The inventor discovered that: 1) Deletion of rbmA in the rugose variant decreased the corrugation of rugose colonies. 2) Complementation of RΔrbmA restored the normal rugose colonial morphology. 3) Vps genes expression is not altered in RΔrbmA and therefore, the less-corrugated colonial morphology of RΔrbmA is due to the loss of RbmA function. 4) It was also determined that RbmA is required for the formation of structurally mature biofilms and for biofilm fitness in V. cholerae.

RbmA does not have any homolog in protein sequence databases. Thus, to gain insight into its possible function, the inventors attempted to determine the likely structure of RbmA using different structure prediction programs. Because preliminary computer predictions and experimental results suggested that RbmA is a secreted protein, structure prediction analysis was conducted based on the assumption that RbmA is secreted and only using the portion of the protein starting with E31, . The inventors used the SAM-T04, protocol for structure prediction, though both local structure prediction and fold recognition are of limited reliability for orphan ORF sequences, as both rely heavily on signals from the sampling of sequence space done by evolution. Five different protein folds were found to have E-values less than 5.0, whereby the top two appeared to be secreted proteins, though their E-values (1.48, and 2.49) indicate that the predictions are speculative at best. The top hit was to 1qfhA, F-actin cross-linking gelation factor (ABP-120) repeats from slime mold (*Dictyostelium discoideum*), which the program SCOP version 1.67, classifies as an E set domain, an immunoglobulin-like beta sandwich possibly related to the immunoglobulin and fibronectin type III domain (FnIIID) superfamilies. This fold family, initially characterized in fibronectin, is common among modular proteins. FnIIID is present in extracellular proteins, intracellular proteins and the extracellular domains of membrane-receptor proteins. FnIIID is also found in some carbohydrases (enzymes that hydrolyse polymers composed of a six-carbon sugar backbone) from different bacteria. Structure analyses of the chitin binding protein, CBP21, from Serratia marcescens and chitinase A1, from *Bacillus circulars*, WL-12, have also revealed the presence of FnIIID in these proteins. The second hit was to 1jlxA, an agglutinin from Love-lies-bleeding (*Amaranthus caudatus*), which SCOP classifies as a beta-trefoil. The beta-trefoil protein family includes fibroblast growth factors, interleukin-1, mannose receptor, agglutinin, and *Clostridium*, neurotoxins. The mannose receptor and agglutinin is a particularly interesting fold, as these proteins are known to bind sugars. Structure prediction suggests that RbmA may fold into either the FnIIID or beta-trefoil family of tertiary structures. Both superfamilies include proteins capable of binding carbohydrates.

Protein localization studies revealed that RbmA is predominantly found in culture supernatants. The size of the approximately 31, kDa immunoreactive polypeptide that was detected in the arabinose-induced CS fraction is consistent with that of the chimeric protein RbmA-Myc without the signal peptide (predicted to be 29, kDa). The main terminal branch (MTB) pathway of the type II general secretion pathway (GSP) is involved in the secretion of several *V. cholerae* proteins, including cholera toxin (CT), heat-labile enterotoxin, endochitinase (ChiA), and protease(s). This pathway may also be involved in the secretion of hemolysin and polysaccharides in *V. cholerae*, . The secretory system by which RbmA translocates is yet to be determined, but it is possible that the MTB pathway plays a role in this process.

In this study, the inventors showed that RbmA is required for the maintenance of rugose colonial morphology and the development of wild type biofilm architecture. Both processes require the production of VPS, which is composed of nearly equal amounts of glucose and galactose, and smaller amounts of N-acetylglucosamine and mannose. Hence, both structure predictions and phenotypic analyses suggest that RbmA may be a sugar-binding protein. The exact mechanism by which this protein functions, (in other words, whether it binds carbohydrates and, if it does, what types) has yet to be determined. It is possible that RbmA binds to carbohydrates in the VPS matrix, thus giving rise to the tightly-packed and organized biofilm structure observed in the wild type rugose variant. It is also possible that RbmA acts like an agglutinin/adhesin, binding cells together or anchoring the biofilm and/or cells to a substratum that contains carbohydrates. Recent studies reported that agglutinin and adhesin proteins are present in *E. coli* and in *Pseudomonas aeruginosa*, . The multipurpose, nonorganelle adhesin TibA mediates cell auto-aggregration, and binding, and invasion of *E. coil*, to human cells, and enhances biofilm formation. Similarly, the two carbohydrate-binding proteins (lectins), LecA and LecB, from *P. aeruginosa*, have been shown to bind specifically to galactose and fucose, respectively. Furthermore, LecB, which localized on the outer membrane of the bacterium, is required for biofilm formation.

In addition to altering biofilm architecture, absence of RbmA reduced the biofilm's resistance to environmental insults. Biofilms formed by RΔrbmA were more sensitive to SDS than wild-type biofilms. Similar finding have also been reported for the biofilms formed by TCP mutant of *V. cholerae*, cultured on chitinous surfaces. These observations suggest that changes to the extra-polymeric substance composition of biofilms, either at the exopolysaccharide or protein level, can alter biofilm fitness.

In *V. cholerae*, several members of the two-component superfamily of proteins are involved in regulating genes required either directly or indirectly for biofilm formation. The positive regulators VpsR and VpsT, which exhibit a high degree of homology to response regulators of the two-component superfamily, are required for the transcription of vps genes and the formation of mature biofilms in *V. cholerae*, . Data in this study show that expression of rbmA, unlike that of vps genes vpsA and vpsL, is positively regulated only by VpsR and not VpsT (FIG. 4). The significance of this result has yet to be determined. A recent study reported that VieA, the response regulator of the VieS/A/B three-component signal transduction system, represses the transcription of rbmA (VC0928, locus) and the vps genes. Interestingly, repression of rbmA in the ΔvieA mutant is observed only in the classical but not in the E1, Tor biotype of *V. cholerae*, presumably because a functionally redundant protein in the E1, Tor biotype compensates for the loss of VieA. HapR, a negative regulator that represses the expression of vps genes at high cell density also negatively regulates rbmA transcription. Altogether, these findings show that genes encoding proteins required for VPS production and biofilm architecture (including rbmA) are coordinately regulated by VpsR and HapR.

EXAMPLE 2

Investigation of the rbmBCDEF Gene Cluster and bap1

A complete description of this research can be found in Fong, J C and Yildiz, F. H. (2007) "The rbmBCDEF Gene Cluster Modulates Development of Rugose Colony Morphology and Biofilm Formation in *Vibrio cholerae*", accepted for publication in Journal of Bacteriology, January, 2007, which is herein incorporated by reference in its entirety to the fullest extent allowed for all purposes.

As discussed above, the inventor discovered that rbmA (VC0928), the first gene located in the vps intergenic region, is required for the full development of wild-type corrugated rugose colony morphology and "typical" pillar and mushroom-like structures of biofilms. The inventor then hypothesized that other genes located in the vps intergenic region may play a similar role in biofilm formation. The inventor generated null mutants of these genes and undertook a complete phenotypic characterization. The results of this investigation show that genes located downstream of rbmA, termed rbmB, rbmC, rbmD, rbmE and rbmF (VC0929-33) encode proteins that modulate rugose colony development and biofilm formation in *V. cholerae*, . In addition, the same research revealed that bap1, (biofilm-associated protein 1) (VC1888) [also called vcp (vps co-regulated protein)], which is located downstream of the vpsII cluster and which has peptide sequence homology to that of rbmC, encodes a protein that is also involved in rugose colony development and biofilm formation in *V. cholerae*.

Materials and Methods for Investigation of the rbmBCDEF Gene Cluster

Bacterial strains, plasmids, and culture conditions and recombinant DNA techniques used were as described above for investigation of RbmA. Primers used in the study of rbmBCDEF and bap1, are listed in Table 3, . Bacterial strains used are listed in Table 2.

Generation of in-frame rbmBCDEF and bap1, deletion mutants and complemented strains. Deletion mutants of rbm-BCDEF and bap1, were generated in the rugose genetic background according to the protocol previously published (Fong et al, 2006, J. Bacteriol. 188:1049-1059). Briefly, 5' regions of the genes were amplified by PCR with deletion primers del_, A and del_, B, while 3' regions of the genes were amplified by PCR with deletion primers del_, C and del_, D (Table 3). The two PCR products generated were then joined via SOEing (splicing by overlap extension) PCR with del_, A and del_, D primers and cloned into pGP704-sacB28, suicide plasmid, resulting in deletion plasmids pFY-271, pFY-272, pFY-273, pFY-274, and pFY-330, for rbmB, rbmC, rbmD, rbmEF and bap1, respectively. The deletion plasmids were maintained in *E. coli* CC118, (λ pir). Bi-parental matings were carried out with *V. cholerae*, rugose variant and the conjugative strain *E. coli*, S17-1, (λ pir) harboring various deletion plasmids. Ampicillin- and rifampicin-resistant transconjugants, resulted from single homologous recombinations, were selected and subjected to sucrose-based selection, similar to that described by Fullner and Mekalanos (Fullner et al, 1999, Infect. Immun. 67:1393-1404). Ampicillin-sensitive and sucrose-resistant *V. cholerae*, deletion strains, which had undergone double homologous recombinations, were selected. Double deletion mutant of rbmC and bap1, was generated by knocking out bap1, in an rbmC deleted rugose strain using the same method described above. The deletion mutants were verified by PCR and designated as RΔrbmB, RΔrbmC, RΔrbmD, RΔrbmEF, RΔbap1, and RΔrbmCΔbap1.

Complementation plasmids prbmB, prbmC, prbmD, prbmEF and pbap1, were constructed by cloning PCR amplified rugose wild-type chromosomal fragments of rbmB, rbmC, rbmD, rbmEF and bap1, (including the up- and downstream regulatory elements) into the vector pACYC177 (New England Biolabs), using respective forward and reverse complementation primers (Table 3). Ampicillin-resistant strains were selected after electroporation of various complementation plasmids into respective deletion strains. Complementation strains were verified via PCR.

Generation of Myc-tagged RbmB, RbmC and Bapl. The coding regions of rbmB, rbmC and Bap1, (including the start codon but excluding the stop codon) were amplified with respective forward and reverse Myc-tagging primers (Table 3) and directionally cloned into the vector pBAD/Myc-His B (Invitrogen), in-frame with the downstream Myc epitope and six histidine codons. The resulting C-terminal Myc-tagged expression plasmids prbmB-myc, prbmC-myc and pbap1-myc were electroporated into RΔrbmB, RΔrbmC and RΔbap1, respectively. Ampicillin-resistant strains harboring the Myc-tagged expression plasmids were selected and verified via PCR. *V. cholerae*, deletion strains carrying the various Myc-tagged expression plasmids were used in cellular fractionation experiments.

Generation of GFP-tagged strains. *V. cholerae*, deletion strains and rugose wild-type variant were tagged with green fluorescent protein (GFP) according to the procedure previously described (Fong et al, 2006). Briefly, tri-parental matings were carried out with donor *E. coli* S17-1, (λ pir) carrying pMCM11, helper *E. coli*, S17-1, (λ pir) harboring pUX-BF13, and various *V. cholerae*, strains. Transconjugants were selected on thiosulfate-citrate-bile salts-sucrose (TCBS, Difco) agar medium containing gentamicin at 30° C. GFP-tagged *V. cholerae*, strains were verified by PCR and used in flow cell experiments.

β-Galactosidase assays. β-galactosidase assays were carried out in MultiScreen®-HA 96-well microtiter plates fitted onto a MultiScreen® filtration system (Millipore) using a previously published procedure (Fong et al, 2006). Exponential cultures were harvested when optical densities at 600, nm ($OD_{600}$) reached 0.3, to 0.5, . The assays were repeated with four different biological replicates and at least eight technical replicates.

Quantitative biofilm assays. Biofilm formation assays were carried out in polyvinyl chloride microtiter plates with 100, μl of 200-fold diluted overnight-grown cultures incubated at 30° C. for 8, h, according to the method previously described (Yildiz, F. et al., 2001, J. Bacteriol. 183:1716-1726). The assays were repeated with three different biological replicates and at least eight technical replicates.

Cell aggregation experiments, flow cell experiments and confocal scanning laser microscopy (CSLM). Cell aggregation experiments were carried out using hanging-drop slides (Fisher Scientific) with 100-fold diluted overnight-grown cultures of GFP-tagged *V. cholerae* strains. Flow cell experiments were carried out according to the procedure previously described (Lim et al, 2006, Mol. Microbiol. 60:331-348). Briefly, overnight-grown cultures of GFP-tagged *V. cholerae*, strains were diluted to $OD_{600}$=0.1, and 350, μl aliquots of the diluted cultures were inoculated by injection into the flow cell chambers. Before inoculation, the chambers were sterilized and equilibrated with 1, liter of 0.5% (vol/vol) hypochlorite, followed by 1, liter of sterile MilliQ water and 200, ml of 2% LB (0.2, g/l tryptone, 0.1, g/l yeast extract, 9, g/l NaCl) at a flow rate of 4.5, ml/h. After inoculation, the chambers were allowed to stand inverted, with no flow, for 1, h. Flow was resumed at a rate of 4.5, ml/h with chambers standing upright for 30, min. Flow cell experiments were carried out at room temperature. CSLM images of the biofilms and cell aggregates were captured with a LSM 5, PASCAL system (Zeiss) at 488, nm excitation and 543, nm emission wavelengths. Three dimensional images of the biofilms were reconstructed using Imaris software (Bitplane). Flow cell and cell aggregates experiments were carried out with at least two different biological replicates.

VPS extractions and analyses. VPS extractions and analyses were carried out according to procedures similar to those previously described (Enos-Berlage et al, 2000, J. Bacteriol. 182:5513-5520). Briefly, overnight-grown cultures (100, μl) were spread on four petri plates (100×15, mm) containing LB agar medium and incubated overnight at 30° C. Bacteria from these plates were harvested by scraping and suspended in 10, ml of phosphate-buffered saline (PBS) (20, mM sodium phosphate [pH 7.3], 100, mm NaCl). Optical densities of the samples were determined after vortexing and the samples were diluted to the same OD with PBS. The normalized samples (10, ml) were transferred to 25-ml Erlenmeyer flasks and shaken on a rotary shaker at 4° C. for 5, h. The VPS suspensions were separated from the cells and debris by repeated centrifugation at 20,000×g for 30, min, followed by 13,000×g for 30, min. Crude VPS was precipitated with 3, volumes of ethanol at 4° C. overnight, followed by centrifugation at 20,000×g for 30, min. The pellets were washed with 70% ethanol and suspended in 3, ml of nuclease buffer (40, mM Tris-Cl [pH 8.0], 10, mm $MgCl_2$, 2, mM $CaCl_2$). DNase I (New England Biolabs) and RNase A (Qiagen) were added to the VPS suspensions at final concentrations of 0.7, units/ml and 5, μg/ml respectively, followed by incubation at 37° C. shaking for 3, h. Proteinase K (Merk) was then added at a final concentration of 70, μg/ml and the suspensions were further incubated shaking overnight at 37° C. VPS suspensions were aliquoted into 2-ml centrifuge tubes and phenol-chloroform extractions (equal volume) were carried out three times, followed by precipitation with 3, volumes of ethanol, washed with 70% ethanol and suspended in 250, μl of water. Equal amount of VPS samples (40, μl) were analyzed by sodium dodecyl sulfate-polyacrylamide gel electrophoresis (SDS-PAGE). The upper (5% polyacrylamide) "stacking" portion of the SDS-PAGE gel was 6.5, cm long, while the lower (12% polyacrylamide) portion of the gel was 2, cm long. The gels were stained with Stains-All (United States Biochemical). VPS analyses were repeated with two different biological replicates.

Cellular fractionations. Overnight-grown cultures of Myc-tagged *V. cholerae*, strains were diluted 200-fold and inoculated into fresh LB medium containing ampicillin. Cells in the exponential growth phase ($OD_{600}$=0.3, to 0.4) were induced with 0.1% (wt/vol) arabinose for 1 h. Cells were harvested by centrifugation at 15,000×g for 15, min, washed with PBS and resuspended in 10, mM Tris-Cl (pH8.0). Cell lysis was carried out with sconication (10×10, sec pulses) and cell debris was separated from whole cell lysate by repeated centrifugation at 15,000×g for 15, min. Culture supernatants were collected by repeated centrifugation at 15,000×g for 15, min, followed by deoxycholic acid sodium salt monohydrate/ trichloroacetic acid (Na-DOC/TCA) precipitation. Briefly, Na-DOC was added to culture supernatants to obtain a final concentration of 0.02% (wt/vol), followed by incubation on ice for 30, min. TCA (Sigma) was then added to obtain a final concentration of 10% (vol/vol), followed by incubation on ice for 2 h. Proteins in the culture supernatants were pelleted by centrifugation at 15,000×g for 30, min. Pellets were washed with ice-cold acetone and resuspended in 10, mM Tris-Cl (pH 8.0). Protein inhibitors aprotinin, leupeptin and pepstatin (Roche) were used at 2, μg/ml, 5, g/ml and 0.7, μg/ml, respectively. Protein concentrations were estimated using a Coomassie Plus protein assay kit (Pierce) with bovine serum albumin as standards. Protein samples were loaded at 40, μg and 5, μg for immunoblot analyses of Myc-tagged proteins (RbmC-Myc and Bapl-Myc) and OmpU, respectively.

Immunoblot analyses. Immunoblot analyses were carried out according to procedure previously described (Fong et al., 2006). Rabbit polyclonal antisera against V. cholerae, OmpU (provided by K. Klose) was used at a dilution of 1:100,000, while mouse monoclonal antibody against the Myc epitope (Santa Cruz Biotechnology) was used at a dilution of 1:1,000, . Horseradish peroxidase-conjugated goat anti-rabbit and anti-mouse secondary antibodies (Santa Cruz Biotechnology) were used at a dilution of 1:2,500, . Immunoblots were developed with the SuperSignal West Pico chemiluminescent kit (Pierce). Immunoblot analyses were carried out with at least two different biological replicates. Immunoblot analyses of the outer membrane protein OmpU was carried out as a control on the cellular fractions.

Results of Investigation of the rbmBCDEF Gene Cluster

RbmB affects rugose colony morphology and biofilm structure formation. RbmB (VC0929) is the second gene located in the vps intergenic region (FIG. 1) and is annotated as a hypothetical protein in The Institute for Genomic Research (TIGR) Comprehensive Microbial Resource (CMR) database. BlastP (NCBI BlastP 2.2.13) searches revealed that RbmB has low peptide sequence similarity to *Alteromonas fortis*, beta-carrageenase CgiA (E-value 1e-05) and *Bacillus circulars*, α-1,3-glucanase Agl (E-value 4e-06); both of which are polysaccharide hydrolases. The similarity of peptide sequences of RbmB and CgiA, calculated using European Molecular Biology Open Source Software Suite (EMBOSS) alignment programs, revealed that RbmB and CgiA exhibit 30.1% similarity over the entire length of the peptide sequences. Similarly, RbmB and Agl exhibit 13.4% similarity over the entire length of the peptide sequences. These findings suggested that rbmB could encode a protein that might function as a polysaccharide hydrolase. To determine the role of rbmB in colony morphology development and biofilm formation, an in-frame deletion mutant of rbmB was generated in the rugose genetic background (RΔrbmB). The deletion mutant exhibited an increased colony corrugation compared to the wild-type rugose and this phenotype was partially complemented (reduced corrugation) by introducing a wild-type copy of rbmB in a multi-copy number plasmid to the RΔrbmB strain (data not shown). Because RΔrbmB exhibited altered colony morphology, we hypothesized that biofilm formation by the mutant may also be altered. To test this hypothesis, we first analyzed total biofilm formation using crystal violet staining assay, but did not observe significant differences in the biofilm forming capacities of RΔrbmB and the rugose wild-type (FIG. 5). We then compared the biofilm structures of these two strains. The biofilm structures of the RΔrbmB mutant developed after 24 h post inoculation differed slightly compared to those of the wild-type. The thickness of the biofilms formed by RΔrbmB was estimated to be 73, μm, while that of the wild-type strain was found to be 65, μm. These results indicate that RbmB affects colony rugosity and subtlety affects 3D biofilm structures. We also compared motility, pellicle formation, growth profiles and cell aggregations of RΔrbmB and the wild-type, but did not observe significant differences.

RbmB affects VPS accumulation and may be a polysaccharide lyase. Because VPS has been linked to rugosity and biofilm formation in *V. cholerae*, (Yildizet al, 1999, . Proc. Natl. Acad. Sci. USA 96:4028-4033), we investigated whether the increased corrugation of the colony morphology and altered biofilm structures in RΔrbmB are due to increased amounts of VPS. To this end, VPS was extracted from RΔrbmB and the wild-type, which were normalized to the same cell density, and the extracted VPS samples were analyzed on a 5% SDS-PAGE and stained with Stains-All. VPS accumulation by the deletion mutant was noticeably higher compared to the wild-type. To determine if this increase was due to an increase in expression of the vps genes in the deletion mutant, we monitored the expression of vpsA and vpsL using vpsA::lacZ and vpsL::lacZ fusion plasmids via β-galactosidase assays. As shown in FIG. 6, there are no significant differences in vpsA and vpsL expression levels between the wild-type and RΔrbmB. Both wild-type and RΔrbmB harboring the vector showed negligible background of β-galactosidase activities (data not shown). Taken together, the results demonstrate that vps gene expressions were not altered in RΔrbmB and that the more-corrugated colony morphology, subtle altered 3D biofilm structures and increased VPS accumulation observed in the deletion mutant are due to the loss of RbmB function.

Computational analyses using Simple Modular Architecture Research Tool (SMART) revealed that RbmB contains six domains composed of parallel alpha-helix repeats (PbH1) (T116-S147, S181-G210, T234-Y256, Y257-P279, W289-S310, and I321-S342), which are often found in enzymes with polysaccharide substrates. ModBase (3D protein models calculated by comparative modeling) software also predicted a right-handed parallel alpha-helix protein fold for RbmB, with an E-value of 6e-19, to 1, rmg, rhamnogalacturonase A from *Aspergillus aculeatus*, . Two putative N-acetylglucosamine and seven putative mannose binding sites were also predicted in RbmB by ModBase. These findings are consistent with the predicted role of RbmB as a polysaccharide lyase in breaking down VPS, which is composed of glucose, galactose, N-acetylglucosamine and mannose, in the extracellular matrix of *V. cholerae*, biofilms.

Polysaccharide lyases reported to date, are (or have been predicted to be) extracellular or periplasmic. TIGR-CMR database indicated the presence of a putative 31-amino acid long signal peptide in RbmB, but SignalP 3.0, (signal peptide cleavage sites prediction) program did not have a strong prediction for a cleavage site (probability of cleavage between S31, and E32, is 0.319, for SignalP-NN method and 0.023, for SignalP-HMM method). We attempted to determine the localization of RbmB with immunoblot analyses using Myc- and His-tagged RbmB. Due to the presence of several contaminating signals around the predicted sizes of the tagged RbmB (45.7 kDa without the predicted signal peptide; 49.9, kDa with the signal peptide) using both anti-Myc and anti-His antibodies, we were unable to determine its cellular localization. We are currently generating anti-RbmB antibodies to determine the localization of this putative polysaccharide lyase.

RbmC and Bapl are required for rugose colony morphology. The third gene in the vps intergenic region is rbmC (VC0930) (FIG. 1), which is predicted to encode a protein exhibiting 46.7% similarity to Bapl (VC1888). Number of studies suggested that these proteins play a role in rugose colony development and biofilm formation in *V. cholerae*, . It was reported that a transposon insertion into VC0930, in an E1, Tor biotype C6706, rugose variant, converts the rugose colony morphology to smooth (Ali et al, 2000, Infect. Immun. 68:6857-6864). Furthermore, Bap1 is required for biofilm formation in the classical biotype O395, strain (Hung et al, 2006, Mol. Microbiol. 59:193-201) and that expressions of both rbmC and bap1, are co-regulated with the vps genes in an E1, Tor biotype A1552, strain (Yildiz et al, 2004, Mol. Microbiol. 53:497-515). To investigate the functions of RbmC and Bap1 in rugosity, we generated in-framed single and double deletions of rbmC and bap1, in the rugose genetic background (RΔrbmC, RΔbap1, and RΔrbmCΔbap1). Although colony morphology of RΔrbmC is not noticeably different than the wild-type rugose variant; RΔbap1, and double deletion RΔrbmCΔbap1, formed colonies that are less corrugated compared to the wild-type. An increase in smoothness is also obvious when comparing RΔbap1, and the double mutant RΔrbmCΔbap1, indicating that RbmC and Bap1 have an additive effect on development of colony corrugation. Partial complementation of the colony morphologies was achieved in RΔbap1, and RΔrbmCΔbap1, carrying the complementation plasmids prbmC and pbap1, suggesting that RbmC and Bap1 may have similar function. Strains carrying the control vector pACYC177 remain less corrugated. Together, these results show that RbmC and Bap1 are required for development of corrugated colonies.

RbmC and Bap1 are secreted proteins and are critical for pellicle and biofilm formation. We next investigated whether pellicle (biofilm formed at the air-liquid interface) and biofilm formation on solid surfaces by the mutants were altered. After 2, days of growth at 30° C. under static condition, the pellicle formed by RΔrbmC is not significantly different to that formed by the wild-type. On the other hand, RΔbap1, formed a pellicle with an altered structure (top panel), while the double deletion mutant RΔrbmCΔbap1, was incapable of forming pellicles. The defect in pellicle formation phenotype of the RΔrbmCΔbap1, mutant could be complemented by introducing the wild-type copy of either rbmC or bap1, on a multi-copy number plasmid, suggesting that RbmC and Bap1 may have similar function. RΔrbmCΔbap1, harboring the control vector pACYC177, remained impaired in pellicle formation. Although total biofilm formation by the two single deletion mutants (RΔrbmC and RΔbap1) were not significantly different compared to the wild-type, the double deletion mutant (RΔrbmCΔbap1) was unable to form biofilms. Using vpsA::lacZ and vpsL::lacZ fusion plasmids, we determined that vps gene expression was not significantly altered in these deletion mutants (FIG. 7), indicating that the observed defect in biofilm formation was not due to decreased vps transcription.

The inventors further investigated biofilm structure formation in these deletion mutants using flow cell systems and CSLM. RΔrbmCΔbap1, formed a thin layer of biofilm, which detached after 6, h. Only a few macrocolonies remained attached to the substratum after 24, h. RΔrbmC formed 3D biofilm structures similar to those of the wild-type at both 6, and 24, h. In contrast, the biofilm structures of RΔbap1, were subtly different than those of the wild-type at both 6, and 24, h. We also extracted and analyzed the VPS from the deletion mutants and the wild-type but did not observe significant differences (data not shown). It should be noted that growth profiles, cell aggregations and motility of the deletion mutants and the wild-type were also similar (data not shown). Together, these results indicate that RbmC and Bap1 are critical for wild-type pellicle and biofilm formation and the observed altered phenotypes are due to the loss of RbmC and Bap1 functions.

SignalP predicted that both RbmC and Bap1 are secreted proteins. RbmC is predicted to contain a signal peptide with cleavage between A22, and T23, (probabilities of 0.806, and 0.870, for the two SignalP methods), while Bap1 is predicted to contain a signal peptide with cleavage between A26, and S27, (probabilities of 0.780, and 0.930). To determine whether RbmC and Bap1 are secreted, we carried out immunoblot analyses using anti-Myc antibodies on proteins in TCA-precipitated culture supernatant (CS) and whole cell lysate (WC) fractions from cultures of RΔrbmC harboring prbmC-myc and RΔbap1, harboring pbap1-myc. Immunoblots of such analysis showed the presence of immunoreactive polypeptides corresponding to the expected sizes for RbmC-Myc (105, kDa) and Bap1-Myc (75.4, kDa) (without the predicted signal peptides) in the CS fractions of the deletion strains harboring their respective over-expression plasmids (lane 1). Such signals were absent in the CS fractions (lane 2) and WC fractions (data not shown) from strains carrying the vector pBAD/Myc-His B. Only weak bands corresponding to the sizes of RbmC-Myc and Bap1-Myc were detected in the WC fractions from strains harboring prbmC-myc or pbap1-myc (data not shown). These results indicate that RbmC and Bap1 are predominantly secreted.

RbmD, RbmE and RbmF are involved in biofilm structure formation and cell aggregation. The last three genes in the vps intergenic region are the 1,317-bp rbmD (VC0931), 288-bp rbmE (VC0932) and 405-bp rbmF (VC0933) (FIG. 1). Since RbmA-C are required for colony morphology and biofilm formation, we hypothesized that RbmD-F may also play similar roles. To investigate this hypothesis, we generated in-frame deletions of rbmD and rbmEF in the rugose genetic background (RΔrbmD and RΔrbmEF). rbmE and rbmF were deleted together as they shared 88, by overlapping coding sequences. RΔrbmD and RΔrbmEF exhibited similar colony morphology as the wild-type. Quantitative biofilm assays and expression analyses of vpsA and vpsL (FIG. 8) did not reveal significant differences between the deletion mutants and the wild-type. Furthermore, we also did not observe significant differences in motility, pellicle formation, growth profiles and VPS accumulation when comparing RΔrbmD, and RΔrbmEF to the wild-type (data not shown).

Analyses of RΔrbmD and RΔrbmEF biofilms formed using flow cell systems revealed that their biofilm structures were different from those of the wild-type. The pillars of the deletion mutants appear to be less-compact compared to those formed by the wild-type at both 6, and 24, h.

The rugose variant forms aggregates when grown in suspension. We compared aggregation phenotypes of the RΔrbmD and RΔrbmEF mutants to that of the wild-type. RΔrbmD formed cell aggregates that are larger and less-compact compared to the wild-type rugose, while RΔrbmEF formed string-like aggregates that were much smaller in size compared to those formed by the wild-type. Complementation of the altered cell aggregation phenotype was achieved with RΔrbmD and RΔrbmEF harboring prbmD and prbmEF respectively (data not shown). Together, these results indicate that RbmD and RbmEF are required for wild-type cell aggregation and biofilm structure formation and that the altered phenotypes are due to the loss of RbmD and RbmEF functions.

TMHMM 2.0, (trans-membrane helices prediction) program predicted twelve trans-membrane helices in RbmD, suggesting that RbmD is located on the membrane. RbmD is also predicted to contain a 30-amino acid signal peptide (probabilities of cleavage between A30, and W31, are 0.390, and 0.666, for the two SignalP methods). Although RbmD is annotated as conserved hypothetical protein in the TIGR-CMR database, Quick BlastP searches and EMBOSS alignment programs revealed that RbmD has peptide sequence similarity to O-antigen polymerases from *Pseudoalteromonas atlantica*, (53.7% similarity) and *Shewanella frigidimarina*, (54.1% similarity), with E-values of 5e-76, and 2e-70, respectively. InterPro (integrated resource of protein families, domains and functional sites) database also indicated the presence of a Wzy_, C domain in RbmD, which is found in O-antigen polymerases involved in the synthesis of the outer membrane lipopolysaccharide O-antigen. It is therefore possible that RbmD is involved in the biosynthesis of VPS in *V. cholerae*, consistent with the observations that RbmD is required for wild-type biofilm structure formation and cell aggregation. In contrast, computational analyses of RbmE and RbmF, which are predicted to be organized in an operon structure, did not reveal significant domain structures. They are annotated as hypothetical proteins in TIGR-CMR database and Quick BlastP searches also did not retrieve protein matches with significant E-values. While RbmE does not contain a signal peptide and is not predicted to be secreted; SignalP predicted RbmF to contain a 22-amino acid signal peptide (probabilities of cleavage between A22, and E23, are 0.890, and 0.999, for the two SignalP methods). The localization and involvement of RbmD-F in VPS biosynthesis in *V. cholerae*, remain to be investigated.

Discussion of Results of Investigation of the rbmBCDEF Gene Cluster

The inventor has already demonstrated that rbmA plays a crucial role in biofilm formation in *V. cholerae*, . In this study, we showed that rbmB, that may encode a putative polysaccharide lyase, is critical for development of wild-type rugose colony morphology and biofilm formation. Deletion of rbmB, which encodes a protein with low sequence homology to polysaccharide hydrolases, resulted in an increase in colony corrugation and accumulation of exopolysaccharides relative to the wild-type. RbmC and its homolog Bapl are predicted to encode proteins with carbohydrate-binding domains. The colonies of rbmC/bap1, double deletion mutant and bap1, single deletion mutant exhibited a decrease in colony corrugation. Furthermore, the rbmC/bap1, double deletion mutant was unable to form biofilms at the air-liquid interface after 2, days, while the biofilms formed on solid surfaces detached readily. Although the colony morphology of rbmDEF mutants was similar to that of the rugose wild-type, their biofilm structure and cell aggregation phenotypes were different than those of the wild-type. Taken together, these results indicate that vps intergenic region genes encode proteins that are involved in *Vibrio*, polysaccharide production and maintenance of biofilm structure and stability.

The deletion mutant, lacking functional RbmB, accumulated more VPS, exhibited larger and thicker mushroom-like biofilm structures, and a more-corrugated colony morphology, suggesting that RbmB modulates these phenotypes by its action on VPS. Consistent with its predicted role as a polysaccharide lyase, computational analyses revealed that RbmB contains six PbH1 domains with a predicted right-handed parallel beta helix protein fold, commonly found in enzymes with polysaccharide substrates, including several bacterial pectate and pectin lyases, fungal and bacterial polygalacturonases and rhamnogalacturonases and carrageenase from *Alteromonas fortis*, . The presence of putative N-acetylglucosamine and mannose binding sites in RbmB further reinforces the notion that RbmB may function as a polysaccharide lyase in *V. cholerae*, breaking down the VPS that is composed of glucose, galactose, N-acetylglucosamine and mannose.

RbmC and its homolog Bapl were previously annotated by TIGR-CMR database as haemolysin-related proteins, and they also share peptide similarity to the haemolysin protein HlyA from *V. cholerae*, . RbmC exhibits 28.2% sequence similarity to HlyA, while the sequence similarity between Bapl and HlyA was found to be 20.7%. However, the fact that transcription of rbmC and bap1, are positively regulated by the positive regulator VpsR and that rbmC and bap1, are co-regulated together with the vps clusters, led us to hypothesize that RbmC and Bapl may have a role in colony morphology and biofilm formation rather than function as haemolysin proteins. Indeed, single deletion of bap1, and double deletions of rbmC and bap1, resulted in strains with less-corrugated colony morphologies and altered pellicle formation. The double deletion mutant was also impaired in forming 3D mature biofilm structures. We also showed that RbmC and Bapl are secreted proteins, consistent with their roles in maintaining rugosity of colony morphology and stabilizing pellicle and biofilm structures.

Ali el al. 2000, (Infect. Immun. 68:6857-6864) reported that a transposon insertion into VC0930 in the chromosome of *V. cholerae*, O1, E1, Tor C6706, rugose variant, converts rugose colony morphology to smooth. However, in-frame deletion of rbmC generated in the O1, E1, Tor A1552 rugose variant in this study did not exhibit altered colony morphology compared to the rugose wild-type, a finding likely to be due to the differences in the genetic make up of these two strains. A study by Hung et al. reported that a bap1, deletion mutant in *V. cholerae*, classical strain O395, was defective in biofilm production. The bap1, deletion mutant generated in *V. cholerae*, O1, E1, Tor A1552, rugose variant in this study was only slightly altered in biofilm formation. The differences could be attributed to the different biotypes used in the studies.

Computational analyses revealed that both RbmC and Bapl contain FG-GAP and carbohydrates-binding domains as well as three putative N-acetylglucosamine binding sites. InterPro database indicated that both RbmC and Bapl contain one possible calcium binding site, two and one FG-GAP domains respectively and one galactose mutarotase-like domain. The FG-GAP domains are found in the extracellular N-terminal region of integrin a chain that has been reported to be involved in ligand-recognition and binding with proteins in the extracellular matrix or surface proteins on other cells. The galactose mutarotase-like domains, on the other hand, are described by Structural Classification of Proteins (SCOP) database as probable carbohydrate-binding domains in enzymes acting on sugars. ModBase software predicted both RbmC and Bapl with a protein fold of 1jv2A (E values of 1e-12, and 5e-14, respectively), a human integrin αV-beta-3. Three putative N-acetylglucosamine binding sites were also predicted in both RbmC and Bapl by ModBase software. Further detail analysis using SAM (Sequence Alignment and Modeling) software revealed that D220-A499, and T640-G821, of RbmC are homologous to the beta-propeller FG-GAP domains of integrin a chain and that the probable carbohydrate-binding domain of RbmC encompasses two homologous sugar-binding lectin domains (Q500-T644, and G821-Y957). These computational predictions are consistent with the roles of RbmC and Bapl in maintaining rugosity of colony morphology and stabilizing pellicle and biofilm structures, possibly through binding to carbohydrates in the extracellular matrix of *V. cholerae*, suggesting that RbmC and Bapl may act as lectins.

Deletion mutants of the last three genes in the vps intergenic region, rbmDEF, did not exhibit significant differences in colony morphology and total biofilm formation relative to the wild-type. However, the mutants are impaired in wild-type biofilm structure formation and cell aggregation, suggesting that the proteins play a role in cell-cell or cell-matrix adhesion. Computational analyses predicted that the putative membrane-bound RbmD contains a Wzy_, C domain found in O-antigen polymerase, suggesting a possible role of RbmD in VPS biosynthesis in *V. cholerae*, . This possibility needs to be further investigated. Computational analyses of RbmE and RbmF, on the other hand, did not reveal significant domain structures or protein matches with significant E-values. Nonetheless, the altered biofilm structures and cell aggregates in RΔbrbmEF, which are similar to those observed with RΔrbmD, suggest that RbmE and RbmF play a role (possibly together with RbmD) in biofilm formation and cell aggregation.

Biofilm formation is widely believed to be employed by many aquatic microorganisms, including *V. cholerae*, as a survival strategy in natural environments and many studies have been carried out to understand the structural and regulatory components of this developmental process. However, the molecular basis of many areas in the biofilm formation and detachment processes remains elusive. Here, we report that the genes rbmA and rbmBCDEF, located in the vps intergenic region, and bap1, are required for biofilm formation in *V. cholerae*. Although the genes in the vps intergenic region are co-regulated with the vps clusters, the presence of putative regulatory elements and their predicted orientations of transcription suggest that they are unlikely a part of the vpsI or vpsII operon structures. We also report possible roles of the proteins encoded by rbmBCDEF and bap1, in the development of rugose-associated phenotypes. Most intriguing are the identification of two possible lectins, RbmC and Bap1, that are required for biofilm stability and identification of a putative polysaccharide lyase that may play a role in degrading VPS in the extracellular matrix, leading to the dissemination of *V. cholerae*, in natural aquatic environmental and the spread of cholera.

In the present disclosure reference is made to particular features of the invention. It is to be understood that the disclosure of the invention in this specification includes all appropriate combinations of such particular features. For example, where a particular feature is disclosed in the context of a particular embodiment or a particular claim, that feature can also be used, to the extent appropriate, in the context of other particular embodiments and claims, and in the invention generally.

The embodiments disclosed in this document are illustrative and exemplary and are not meant to limit the invention. Other embodiments can be utilized and structural changes can be made without departing from the scope of the claims of the present invention. As used herein and in the appended claims, the singular forms "a", "an", and "the" include plural reference unless the context clearly dictates otherwise. Thus, for example, a reference to "a part" includes a plurality of such parts, and so forth.

---

The invention claimed is:

1. A method for reducing colonization by *vibrio cholerae* on a surface, the method comprising: reducing the expression of a polynucleotide selected from the group consisting of: rbmA, rbmB, rbmC, rbmD, rbmE, and rbmF, the method comprising administering an agent to *Vibrio cholerae* on a surface, the agent comprising a small interfering RNA (siRNA) molecule, wherein the small interfering RNA (siRNA) molecule interferes with expression of rbmA, rbmB, rbmC, rbmD, rbmE or rbmF.

2. The method of claim 1 comprising contacting to said *Vibrio cholerae* a small interfering RNA (siRNA) molecule, wherein the small interfering RNA (siRNA) molecule consists of an siRNA that interferes with expression of rbmA.

3. The method of claim 1 comprising contacting to said *Vibrio cholerae* a small interfering RNA (siRNA) molecule, wherein the small interfering RNA (siRNA) molecule consists of an siRNA that interferes with expression of rbmB.

4. The method of claim 1 comprising contacting to said *Vibrio cholerae* a small interfering RNA (siRNA) molecule, wherein the small interfering RNA (siRNA) molecule consists of an siRNA that interferes with expression of rbmC.

5. The method of claim 1 comprising contacting to said *Vibrio cholerae* a small interfering RNA (siRNA) molecule, wherein the small interfering RNA (siRNA) molecule consists of an siRNA that interferes with expression of rbmD.

6. The method of claim 1 comprising contacting to said *Vibrio cholerae* a small interfering RNA (siRNA) molecule, wherein the small interfering RNA (siRNA) molecule consists of an siRNA that interferes with expression of rbmE.

7. The method of claim 1 comprising contacting to said *Vibrio cholerae* a small interfering RNA (siRNA) molecule, wherein the small interfering RNA (siRNA) molecule consists of an siRNA that interferes with expression of rbmF.

8. The method of claim 1 wherein the surface is a gastro-intestinal surface.

9. The method of claim 8 wherein the method results in altered biofilm formation on a gastro-intestinal surface.

10. The method of claim 1 wherein said siRNA is provided exogenously, via a vector.

11. The method of claim 1 wherein said siRNA is produced endogenously.

12. The method of claim 11 wherein said siRNA is produced endogenously by RNAse III ribonuclease.

13. The method of claim 1 wherein said siRNA is of 20-25 nucleotides in length.

* * * * *

SEQUENCE LISTING

```
<160> NUMBER OF SEQ ID NOS: 49

<210> SEQ ID NO 1
<211> LENGTH: 30
<212> TYPE: DNA
<213> ORGANISM: Artificial Sequence
<220> FEATURE:
<223> OTHER INFORMATION: primer VC0928_del_A

<400> SEQUENCE: 1
gatctctaga ctgtttgtgg cgatcacatc                                    30

<210> SEQ ID NO 2
<211> LENGTH: 30
<212> TYPE: DNA
<213> ORGANISM: Artificial Sequence
<220> FEATURE:
<223> OTHER INFORMATION: primer VC0928_del_B

<400> SEQUENCE: 2
cagaaacaat acaactggcg ctaaggctaa                                    30

<210> SEQ ID NO 3
<211> LENGTH: 30
<212> TYPE: DNA
<213> ORGANISM: Artificial Sequence
<220> FEATURE:
<223> OTHER INFORMATION: primer VC0928_del_C

<400> SEQUENCE: 3
cgccagttgt attgtttctg gtgagcgagt                                    30

<210> SEQ ID NO 4
<211> LENGTH: 31
```

```
<212> TYPE: DNA
<213> ORGANISM: Artificial Sequence
<220> FEATURE:
<223> OTHER INFORMATION: primer VC0928_del_D

<400> SEQUENCE: 4
gatcccatgg tcgtttcttt cgaacatgtc a                              31

<210> SEQ ID NO 5
<211> LENGTH: 33
<212> TYPE: DNA
<213> ORGANISM: Artificial Sequence
<220> FEATURE:
<223> OTHER INFORMATION: primer VC0928_com F

<400> SEQUENCE: 5
gatcaagctt tttggtttat ttttgctttc tgg                            33

<210> SEQ ID NO 6
<211> LENGTH: 30
<212> TYPE: DNA
<213> ORGANISM: Artificial Sequence
<220> FEATURE:
<223> OTHER INFORMATION: primer VC0928_com R

<400> SEQUENCE: 6
gatcctcgag tgaggaaagc ggtaaactcc                                30

<210> SEQ ID NO 7
<211> LENGTH: 36
<212> TYPE: DNA
<213> ORGANISM: Artificial Sequence
<220> FEATURE:
<223> OTHER INFORMATION: primer VC0928myc F

<400> SEQUENCE: 7
gatcctcgag gttgtctaac tttaaaggat ctatca                         36

<210> SEQ ID NO 8
<211> LENGTH: 36
<212> TYPE: DNA
<213> ORGANISM: Artificial Sequence
<220> FEATURE:
<223> OTHER INFORMATION: primer VC0928myc R

<400> SEQUENCE: 8
gatctctaga tttttttta ccactgtcat tgactg                          36

<210> SEQ ID NO 9
<211> LENGTH: 32
<212> TYPE: DNA
<213> ORGANISM: Artificial Sequence
<220> FEATURE:
<223> OTHER INFORMATION: primer P0928 F1

<400> SEQUENCE: 9
gatcgaattc gttacaagaa cccggaagaa tg                             32

<210> SEQ ID NO 10
<211> LENGTH: 36
<212> TYPE: DNA
<213> ORGANISM: Artificial Sequence
<220> FEATURE:
<223> OTHER INFORMATION: primer P0928 R1

<400> SEQUENCE: 10
gatcggatcc ccatttgttt ttacaactgg cgctaa                         36
```

<210> SEQ ID NO 11
<211> LENGTH: 30
<212> TYPE: DNA
<213> ORGANISM: Artificial Sequence
<220> FEATURE:
<223> OTHER INFORMATION: primer rbmB_del_A

<400> SEQUENCE: 11
gatctctaga gtgagcgagt ggaacagtca                              30

<210> SEQ ID NO 12
<211> LENGTH: 32
<212> TYPE: DNA
<213> ORGANISM: Artificial Sequence
<220> FEATURE:
<223> OTHER INFORMATION: primer rbmB_del_B

<400> SEQUENCE: 12
gaacgcattt ctcgtttctt tcgaacatgt ca                           32

<210> SEQ ID NO 13
<211> LENGTH: 31
<212> TYPE: DNA
<213> ORGANISM: Artificial Sequence
<220> FEATURE:
<223> OTHER INFORMATION: primer rbmB_del_C

<400> SEQUENCE: 13
aagaaacgag aaatgcgttc gaatcatcct c                            31

<210> SEQ ID NO 14
<211> LENGTH: 30
<212> TYPE: DNA
<213> ORGANISM: Artificial Sequence
<220> FEATURE:
<223> OTHER INFORMATION: primer rbmB_del_D

<400> SEQUENCE: 14
gatcccatgg gaccgacagc aagtgcaata                              30

<210> SEQ ID NO 15
<211> LENGTH: 31
<212> TYPE: DNA
<213> ORGANISM: Artificial Sequence
<220> FEATURE:
<223> OTHER INFORMATION: primer rbmC_del_A

<400> SEQUENCE: 15
gatctctaga agctgggcta aacagaacaa g                            31

<210> SEQ ID NO 16
<211> LENGTH: 30
<212> TYPE: DNA
<213> ORGANISM: Artificial Sequence
<220> FEATURE:
<223> OTHER INFORMATION: primer rbmC_del_B

<400> SEQUENCE: 16
taatcgccac caggcggctg ataatacacc                              30

<210> SEQ ID NO 17
<211> LENGTH: 32
<212> TYPE: DNA
<213> ORGANISM: Artificial Sequence
<220> FEATURE:
<223> OTHER INFORMATION: primer rbmC_del_C

```
<400> SEQUENCE: 17
cagccgcctg gtggcgatta aattcacgat gc                                32

<210> SEQ ID NO 18
<211> LENGTH: 30
<212> TYPE: DNA
<213> ORGANISM: Artificial Sequence
<220> FEATURE:
<223> OTHER INFORMATION: primer rbmC_del_D

<400> SEQUENCE: 18
gatcccatgg ggcagtttaa tggcgatcat                                   30

<210> SEQ ID NO 19
<211> LENGTH: 30
<212> TYPE: DNA
<213> ORGANISM: Artificial Sequence
<220> FEATURE:
<223> OTHER INFORMATION: primer rbmD_del_A

<400> SEQUENCE: 19
gatctctaga gaaggatggc tctagcgtgt                                   30

<210> SEQ ID NO 20
<211> LENGTH: 30
<212> TYPE: DNA
<213> ORGANISM: Artificial Sequence
<220> FEATURE:
<223> OTHER INFORMATION: primer rbmD_del_Be

<400> SEQUENCE: 20
caatgaaatt ggcagtttaa tggcgatcat                                   30

<210> SEQ ID NO 21
<211> LENGTH: 31
<212> TYPE: DNA
<213> ORGANISM: Artificial Sequence
<220> FEATURE:
<223> OTHER INFORMATION: primer rbmD_del_C

<400> SEQUENCE: 21
ttaaactgcc aatttcattg agcgaccatg c                                 31

<210> SEQ ID NO 22
<211> LENGTH: 30
<212> TYPE: DNA
<213> ORGANISM: Artificial Sequence
<220> FEATURE:
<223> OTHER INFORMATION: primer rbmD_del_D

<400> SEQUENCE: 22
gatcgagctc ggacccaacc gagattatca                                   30

<210> SEQ ID NO 23
<211> LENGTH: 30
<212> TYPE: DNA
<213> ORGANISM: Artificial Sequence
<220> FEATURE:
<223> OTHER INFORMATION: primer rbmEF_del_A

<400> SEQUENCE: 23
gatctctaga caactttgca tccaagacca                                   30

<210> SEQ ID NO 24
<211> LENGTH: 30
```

```
<212> TYPE: DNA
<213> ORGANISM: Artificial Sequence
<220> FEATURE:
<223> OTHER INFORMATION: primer rbmEF_del_B

<400> SEQUENCE: 24
ttcatttgat ccgggcttaa ccaatacctt                                            30

<210> SEQ ID NO 25
<211> LENGTH: 32
<212> TYPE: DNA
<213> ORGANISM: Artificial Sequence
<220> FEATURE:
<223> OTHER INFORMATION: primer rbmEF_del_C

<400> SEQUENCE: 25
ttaagcccgg atcaaatgaa gcggtagtgt tt                                         32

<210> SEQ ID NO 26
<211> LENGTH: 32
<212> TYPE: DNA
<213> ORGANISM: Artificial Sequence
<220> FEATURE:
<223> OTHER INFORMATION: primer rbmEF_del_D

<400> SEQUENCE: 26
gatcgagctc gaaaccaatt gaaaacaacc aa                                         32

<210> SEQ ID NO 27
<211> LENGTH: 30
<212> TYPE: DNA
<213> ORGANISM: Artificial Sequence
<220> FEATURE:
<223> OTHER INFORMATION: primer bap1_del_A

<400> SEQUENCE: 27
ctatgagctc gctacctccc gtctgtttca                                            30

<210> SEQ ID NO 28
<211> LENGTH: 31
<212> TYPE: DNA
<213> ORGANISM: Artificial Sequence
<220> FEATURE:
<223> OTHER INFORMATION: primer bap1_del_B

<400> SEQUENCE: 28
gcggaacgcg ctgtttcatg gcttgacctt c                                          31

<210> SEQ ID NO 29
<211> LENGTH: 31
<212> TYPE: DNA
<213> ORGANISM: Artificial Sequence
<220> FEATURE:
<223> OTHER INFORMATION: primer bap1_del_C

<400> SEQUENCE: 29
catgaaacag cgcgttccgc tgaagtaaag a                                          31

<210> SEQ ID NO 30
<211> LENGTH: 30
<212> TYPE: DNA
<213> ORGANISM: Artificial Sequence
<220> FEATURE:
<223> OTHER INFORMATION: primer bap1_del_D

<400> SEQUENCE: 30
ctagtctaga agcttcggct ttaacccaat                                            30
```

```
<210> SEQ ID NO 31
<211> LENGTH: 30
<212> TYPE: DNA
<213> ORGANISM: Artificial Sequence
<220> FEATURE:
<223> OTHER INFORMATION: primer rbmB_com F

<400> SEQUENCE: 31
gatccccggg gtgagcgagt ggaacagtca                                    30

<210> SEQ ID NO 32
<211> LENGTH: 30
<212> TYPE: DNA
<213> ORGANISM: Artificial Sequence
<220> FEATURE:
<223> OTHER INFORMATION: primer rbmB_com R

<400> SEQUENCE: 32
gatcctcgag gaccgacagc aagtgcaata                                    30

<210> SEQ ID NO 33
<211> LENGTH: 30
<212> TYPE: DNA
<213> ORGANISM: Artificial Sequence
<220> FEATURE:
<223> OTHER INFORMATION: primer rbmC_com F

<400> SEQUENCE: 33
gatccccggg ctagaaaatg cttcttgaaa                                    30

<210> SEQ ID NO 34
<211> LENGTH: 27
<212> TYPE: DNA
<213> ORGANISM: Artificial Sequence
<220> FEATURE:
<223> OTHER INFORMATION: primer rbmC_com R

<400> SEQUENCE: 34
gatcctcgag ttgctcttca tctcctg                                       27

<210> SEQ ID NO 35
<211> LENGTH: 27
<212> TYPE: DNA
<213> ORGANISM: Artificial Sequence
<220> FEATURE:
<223> OTHER INFORMATION: primer rbmD_com F

<400> SEQUENCE: 35
gatccccggg cgactcatcg ctttact                                       27

<210> SEQ ID NO 36
<211> LENGTH: 27
<212> TYPE: DNA
<213> ORGANISM: Artificial Sequence
<220> FEATURE:
<223> OTHER INFORMATION: primer rbmD_com R

<400> SEQUENCE: 36
gatcctcgag cccagataac tgacttg                                       27

<210> SEQ ID NO 37
<211> LENGTH: 30
<212> TYPE: DNA
<213> ORGANISM: Artificial Sequence
<220> FEATURE:
<223> OTHER INFORMATION: primer rbmEF_com F
```

<400> SEQUENCE: 37
gatcaagctt caactttgca tccaagacca         30

<210> SEQ ID NO 38
<211> LENGTH: 32
<212> TYPE: DNA
<213> ORGANISM: Artificial Sequence
<220> FEATURE:
<223> OTHER INFORMATION: primer rbmEF_com R

<400> SEQUENCE: 38
gatcctcgag gaaaccaatt gaaaacaacc aa         32

<210> SEQ ID NO 39
<211> LENGTH: 27
<212> TYPE: DNA
<213> ORGANISM: Artificial Sequence
<220> FEATURE:
<223> OTHER INFORMATION: primer bap1_com F

<400> SEQUENCE: 39
gatccccggg gactcgatcg tgagttt         27

<210> SEQ ID NO 40
<211> LENGTH: 32
<212> TYPE: DNA
<213> ORGANISM: Artificial Sequence
<220> FEATURE:
<223> OTHER INFORMATION: primer bap1_com R

<400> SEQUENCE: 40
gatcaagctt ggtttattcc tttatctttt ta         32

<210> SEQ ID NO 41
<211> LENGTH: 30
<212> TYPE: DNA
<213> ORGANISM: Artificial Sequence
<220> FEATURE:
<223> OTHER INFORMATION: primer rbmB_myc F

<400> SEQUENCE: 41
gatcctcgag ggtgctgtta tacttaaatc         30

<210> SEQ ID NO 42
<211> LENGTH: 33
<212> TYPE: DNA
<213> ORGANISM: Artificial Sequence
<220> FEATURE:
<223> OTHER INFORMATION: primer rbmB_myc R

<400> SEQUENCE: 42
gatcgaattc catctttaat aaagtgctgt ata         33

<210> SEQ ID NO 43
<211> LENGTH: 30
<212> TYPE: DNA
<213> ORGANISM: Artificial Sequence
<220> FEATURE:
<223> OTHER INFORMATION: primer rbmC_myc F

<400> SEQUENCE: 43
gatcctcgag aatgacgtct cactatattg         30

<210> SEQ ID NO 44
<211> LENGTH: 28

-continued

<212> TYPE: DNA
<213> ORGANISM: Artificial Sequence
<220> FEATURE:
<223> OTHER INFORMATION: primer rbmC_myc  R

<400> SEQUENCE: 44
gatcgaattc cgtagacaaa ctggaagc                                              28

<210> SEQ ID NO 45
<211> LENGTH: 30
<212> TYPE: DNA
<213> ORGANISM: Artificial Sequence
<220> FEATURE:
<223> OTHER INFORMATION: primer bap1_myc  F

<400> SEQUENCE: 45
gatcgaattc atgaaacaga caaaaacgtt                                            30

<210> SEQ ID NO 46
<211> LENGTH: 26
<212> TYPE: DNA
<213> ORGANISM: Artificial Sequence
<220> FEATURE:
<223> OTHER INFORMATION: primer bap1_myc  R

<400> SEQUENCE: 46
gatctctaga cgcttcagcg gaacgc                                                26

<210> SEQ ID NO 47
<211> LENGTH: 12
<212> TYPE: PRT
<213> ORGANISM: Vibrio cholerae
<220> FEATURE:
<223> OTHER INFORMATION: protein spot 1

<400> SEQUENCE: 47

Glu Gly Glu Ala Asn Val Glu Phe Trp Met Thr Ala
  1               5                  10

<210> SEQ ID NO 48
<211> LENGTH: 271
<212> TYPE: PRT
<213> ORGANISM: Vibrio cholerae
<220> FEATURE:
<223> OTHER INFORMATION: strain El Tor N16961 hypothetical protein
      VC0928

<400> SEQUENCE: 48

Met Ser Asn Phe Lys Gly Ser Ile Met Asn Lys Arg His Tyr Tyr
  1               5                  10                  15

Leu Ala Ser Cys Leu Ala Leu Leu Phe Ser Thr Ala Ser Tyr Ala
                 20                  25                  30

Glu Val Asp Cys Glu Leu Gln Pro Val Ile Glu Ala Asn Leu Ser
             35                  40                      45

Leu Asn Gln Asn Gln Leu Ala Ser Asn Gly Gly Tyr Ile Ser Ser
         50                  55                      60

Gln Leu Gly Ile Arg Asn Glu Ser Cys Glu Thr Val Lys Phe Lys
     65                      70                      75

Tyr Trp Leu Ser Ile Lys Gly Pro Glu Gly Ile Tyr Phe Pro Ala
         80                  85                      90

Lys Ala Val Val Gly Val Asp Thr Ala Gln Gln Glu Ser Asp Ala
         95                 100                     105

Leu Thr Asp Gly Arg Met Leu Asn Val Thr Arg Gly Phe Trp Val
        110                 115                     120

```
Pro Glu Tyr Met Ala Asp Gly Lys Tyr Thr Val Ser Leu Gln Val
            125                 130                 135

Val Ala Glu Asn Gly Lys Val Phe Lys Ala Asn Gln Glu Phe Val
            140                 145                 150

Lys Gly Val Asp Leu Asn Ser Leu Pro Glu Leu Asn Gly Leu Thr
            155                 160                 165

Ile Asp Ile Lys Asn Gln Phe Gly Ile Asn Ser Val Glu Ser Thr
            170                 175                 180

Gly Gly Phe Val Pro Phe Thr Val Asp Leu Asn Asn Gly Arg Glu
            185                 190                 195

Gly Glu Ala Asn Val Glu Phe Trp Met Thr Ala Val Gly Pro Asp
            200                 205                 210

Gly Leu Ile Ile Pro Val Asn Ala Arg Glu Lys Trp Val Ile Ala
            215                 220                 225

Ser Gly Asp Thr Tyr Ser Lys Val Arg Gly Ile Asn Phe Asp Lys
            230                 235                 240

Ser Tyr Pro Ala Gly Glu Tyr Thr Ile Asn Ala Gln Val Val Asp
            245                 250                 255

Ile Val Ser Gly Glu Arg Val Glu Gln Ser Met Thr Val Val Lys
            260                 265                 270

Lys
```

<210> SEQ ID NO 49
<211> LENGTH: 816
<212> TYPE: DNA
<213> ORGANISM: Vibrio cholerae
<220> FEATURE:
<223> OTHER INFORMATION: gene locus VC0928 rbmA

<400> SEQUENCE: 49

```
ttgtctaact ttaaaggatc tatcatgaac aaacgtcatt attatctggc ctcatgcttg      60
gcattgttat tttcaacggc ttcttatgcg gaagtggatt gtgagttaca gccagtgatt     120
gaagcaaatc tttcattaaa tcaaaaccag ttggcaagta acggtggata catctctagt     180
cagctaggga tccgtaatga aagctgtgaa acagtgaagt tcaaatactg ctatcgatt      240
aaaggtccag aaggtatcta cttcccagcc aaagcggtag ttggagttga tacagcgcag     300
caagagtctg atgctcttac tgatggtcgt atgttgaacg ttacacgtgg tttctgggtt     360
ccagagtata tggctgatgg taaatatact gtttctcttc aagtcgttgc agaaaatgga     420
aaagtattta agccaaccaa agaatttgtg aaaggagtcg atttaaatag cctacctgaa     480
ctcaatggtt tgactattga tatcaaaaat caatttggca ttaatagtgt ggaaagtacc     540
ggcggttttg ttccattcac cgttgattta aataatggcc gcgagggaga agctaacgtc     600
gagttctgga tgactgcggt aggtcctgat ggtttgatta ttcctgtcaa tgcgagagag     660
aaatgggtta ttgcttcagg tgatacttat tcaaaagtgc gtggtattaa ttttgataaa     720
agctatccag cgggcgaata cacaattaat gctcaagtgg tagacattgt ttctggtgag     780
cgagtggaac agtcaatgac agtggtaaaa aaataa                                816
```